(12) United States Patent
Hancock et al.

(10) Patent No.: US 7,972,606 B2
(45) Date of Patent: Jul. 5, 2011

(54) **T24 ANTIGEN FOR IMMUNODIAGNOSIS OF *TAENIA SOLIUM* CYSTICERCOSIS**

(75) Inventors: Kathy Hancock, Atlanta, GA (US); Fatima Williams Whitfield, Newark, DE (US); Melinda L. Yushak, Decatur, GA (US); Sowmya Pattabhi, Smyrna, GA (US); Victor C.W. Tsang, Decatur, GA (US)

(73) Assignee: The United States of America as respresented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 12/431,928

(22) Filed: Apr. 29, 2009

(65) Prior Publication Data

US 2009/0209470 A1 Aug. 20, 2009

Related U.S. Application Data

(62) Division of application No. 10/557,265, filed as application No. PCT/US2004/015041 on May 13, 2004, now Pat. No. 7,547,762.

(60) Provisional application No. 60/471,950, filed on May 19, 2003.

(51) Int. Cl.
*C07K 1/00* (2006.01)
*C07K 14/00* (2006.01)
*C07K 17/00* (2006.01)
*C12N 15/09* (2006.01)
*A61K 39/02* (2006.01)
*A61K 39/00* (2006.01)
*A61K 39/002* (2006.01)
*G01N 33/53* (2006.01)
*G01N 33/569* (2006.01)

(52) U.S. Cl. .................. 424/200.1; 424/265.1; 435/7.1; 435/7.22; 435/69.3; 530/350

(58) Field of Classification Search ........................ None
See application file for complete search history.

(56) References Cited

U.S. PATENT DOCUMENTS

| | | | |
|---|---|---|---|
| 4,740,456 A | 4/1988 | Kuhn et al. | |
| 4,801,532 A | 1/1989 | Kuhn et al. | |
| 5,354,660 A | 10/1994 | Tsang et al. | |
| 5,874,251 A | 2/1999 | Zarlenga, Jr. et al. | |
| 6,156,505 A | 12/2000 | Steinbruch et al. | |
| 6,331,388 B1 | 12/2001 | Malkovsky et al. | |
| 6,379,906 B1 | 4/2002 | Tsang et al. | |

FOREIGN PATENT DOCUMENTS

WO   WO 01/10897 A2   2/2001

OTHER PUBLICATIONS

Greenspan et al. (Nature Biotechnology 7: 936-937, 1999).*

Colman et al. (Research in Immunology 145: 33-36, 1994, p. 33 col. 2, p. 35 col. 1).*
GenBank Accession No. BF643023 (Dec. 19, 2000).
GenBank Accession No. BQ173191 (Sep. 18, 2002).
Bowie et al., "Deciphering the Message in Protein Sequences: Tolerance to Amino Acid Substitutions," *Science* 247:1306-1310, 1990.
de Aluja et al., "Experimental *Taenia solium* Cysticercosis in Pigs: Characteristics of the Infection and Antibody Response," *Vet. Parasitol.* 61:49-59 (1996).
Gerhold et al., "It's the Genes! EST Access to Human Genome Content," *BioEssays* 18:973-981, 1996.
Gonzalez et al., "Protection of Pigs with Cysticercosis from Further Infections After Treatment with Oxfendazole," *Am. J. Trop. Med. Hyg.* 65:15-18, 2001.
Greene et al., "*Taenia solium*: Molecular Cloning and Serologic Evaluation of 14- and 18-KDA Related, Diagnostic Antigens," *J. Parasitol.* 86:1001-1007 (2000).
Greenspan et al., "Defining Epitopes: It's Not as Easy as it Seems," *Nature Biotechnology* 17:936-937, 1999.
Hancock et al., "Characterization of Six Proteins, Diagnostic for Cysticercosis," *Abstracts of the General Meeting of the American Society for Microbiology and ASM 102$^{nd}$ General Meeting* 102:127 (2002).
Hancock et al., "Characterization of the 8-Kilodalton Antigens of *Taenia solium* Metacestodes and Evaluation of Their Use in an Enzyme-Linked Immunosorbent Assay for Serodiagnosis," *J. Clin. Microbiol.* 41:2577-2586, 2003.
Hancock et al., "Characterization and Cloning of T24, a *Taenia solium* Antigen Diagnostic for Cysticercosis," *Mol. Biochem. Parasitol.* 147:109-117, 2006.
Ito et al., "Recent Advances in Basic and Applied Science for the Control of Taeniasis/Cysticercosis in Asia," *Southeast Asian J. Trop. Med. Public Health* 33:79-82 (2002).
Maniatis et al. Molecular Cloning; Laboratory Manual Chapter 12, 1989.
Plancarte et al., "Reactivity in Elisa and Dot Blot of Purified GP24, an Immunodominant Antigen of *Taenia solium*, for the Diagnosis of Human Neurocysticercosis," *Int J. Parasitol.* 24:733-738, 1994.
Plancarte et al., "Characterization of GP39-42 and GP24 Antigens from *Taenia solium* Cysticerci and their Antigenic GP10 Subunit," *Parasitol. Res.* 85:680-684 (1999).
Plancarte et al., "Vaccination Against *Taenia solium* Cysticercosis in Pigs Using Native and Recombinant Oncosphere Antigens ," *Int. J. Parasitol.* 29:643-647, 1999.
Sotelo et al., "Review of Neurocysticercosis," *Neurosurg. Focus* 12:1-7, 2002.

* cited by examiner

*Primary Examiner* — Robert A Zeman
*Assistant Examiner* — Nina A Archie
(74) *Attorney, Agent, or Firm* — Klarquist Sparkman, LLP

(57) ABSTRACT

The present disclosure relates to T24 nucleic acid sequences, amino acid sequences, and antibodies. Methods for detecting and diagnosing *Taenia solium* infection in a subject using the T24 sequences and specific binding agents are also disclosed. The T24 sequences disclosed herein can be formulated into a pharmaceutical composition for administration to a subject. For example, the disclosed T24 polypeptides can also be administered to a subject to stimulate an immune response in the subject, thereby protecting the subject against *T. solium* infection.

11 Claims, 1 Drawing Sheet

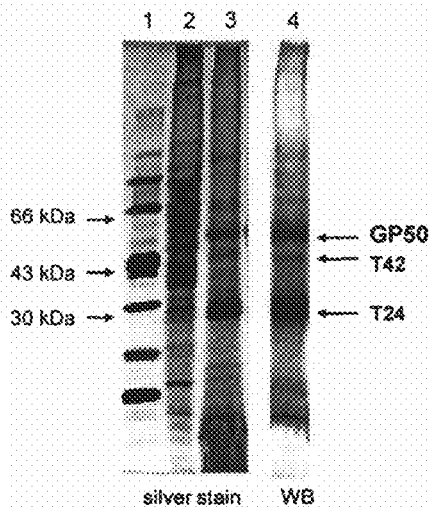
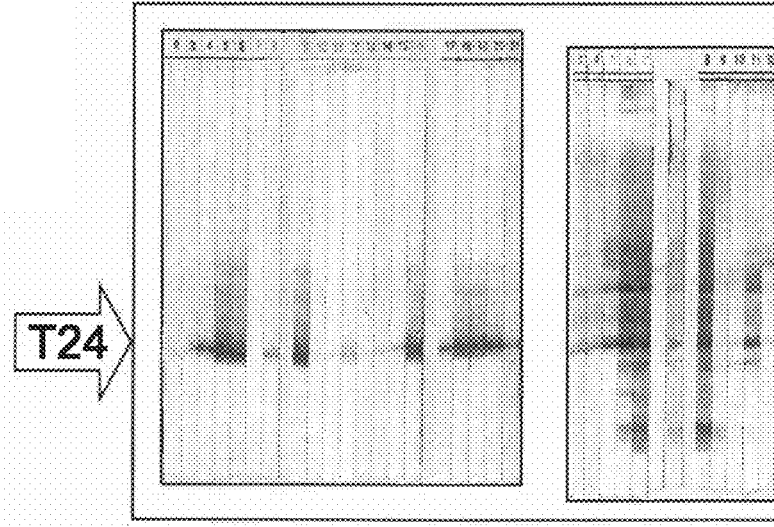

T24 ANTIGEN FOR IMMUNODIAGNOSIS OF *TAENIA SOLIUM* CYSTICERCOSIS

CROSS-REFERENCE TO RELATED APPLICATIONS

This is a divisional of U.S. application Ser. No. 10/557,265, filed Nov. 18, 2005, now U.S. Pat. No. 7,547,762 issued on Jun. 16, 2009, which is the U.S. National Stage of International Application No. PCT/US2004/015041, filed May 13, 2004 (published in English under PCT Article 21(2)), which in turn claims the benefit of U.S. Provisional Application No. 60/471,950 filed May 19, 2003, herein incorporated by reference in its entirety.

FIELD

This application relates to purified *Taenia solium* T24 sequences and uses thereof in the diagnosis and prevention of cysticercosis and neurocysticercosis.

BACKGROUND

The disease cysticercosis, caused by the larval form of *Taenia solium*, is endemic in all regions of the world where humans and pigs live in close contact. The lifecycle of *T. solium* begins when swine, the intermediate hosts, ingest tapeworm eggs excreted in the feces of a tapeworm carrier. The larvae hatch from the eggs and invade most tissues of the swine, giving rise to the disease cysticercosis.

When humans ingest raw or undercooked meat from cysticercotic swine, tapeworms, or taeniasis, develop. Patients with taeniasis may exhibit epigastric discomfort, nausea, irritability, diarrhea, and weight loss. In addition, proglottids, or individual segments of the tapeworm that are self-contained hermaphroditic reproductive units, may obstruct the appendix, biliary duct, or pancreatic duct.

Humans may also ingest *T. solium* eggs present in contaminated food and water and become infected with the larval form. After *T. solium* eggs are ingested, cysticerci may develop in the subcutaneous tissues, muscles, heart, lungs, liver, brain, and eye. Although small numbers of viable cysticerci may fail to produce symptoms in the infected host, death of the larvae stimulate a marked inflammatory reaction, fever, muscle pains, and eosinophilia. If the larvae invade the central nervous system, a single cyst may cause disease. The host may develop meningoencephalitis, epileptic seizures, dementia and other neurologic or psychiatric manifestations, and death can result from acute intracranial hypertension. The various manifestations of neurologic dysfunction caused by *T. solium* infection are collectively termed neurocysticercosis. *T. solium* neurocysticercosis has a current worldwide toll of 50 million cases with 50,000 deaths each year. Although neurocysticercosis is rarely acquired in the United States, it is common in Latin America, Asia, sub-Saharan Africa, and Eastern Europe. Due to the increased travel and immigration from highly endemic areas, detection and treatment of *T. solium* related diseases are U.S. public health priorities.

Diagnosis of cysticercosis historically relied on histological identification of the parasite by biopsy or autopsy. Although radiologic methods such as computed tomography or nuclear magnetic resonance imaging are useful in diagnosing neurocysticercosis, they are often too expensive or inaccessible in developing countries. In addition, although serological diagnostic tests are available to identify *T. solium* infection and diagnose neurocysticercosis, current immunoelectrotransfer blot (EITB) assays utilize purified, naturally-occurring *T. solium* larval proteins, making the assay reagents expensive and difficult to produce (see U.S. Pat. No. 5,354,660 to Tsang et al.).

In developing countries where *T. solium* related diseases are endemic, access to diagnostic assays can be limited due to the high cost of using *T. solium* antigens that are produced using complicated purification procedures. Furthermore, because cysticercosis is most prevalent in rural areas of developing countries, a field test is needed for epidemiological studies and surveillance. A field assay using inexpensive and reliable reagents would be an important tool in breaking the transmission cycle of the parasite, enabling the on-site diagnosis of infected pigs and immediate treatment with antihelminthic agents such as oxfendazole. A field diagnosis of cysticercosis would also serve as an economic benefit to pig farmers, because uninfected pigs command a higher price.

Therefore, there is a need to clone the *T. solium* glycoproteins so that recombinant proteins can be readily produced for field testing and diagnosis of cysticercosis and neurocysticercosis.

SUMMARY

In order to develop a simple detection assay for field use, the *T. solium* T24 diagnostic protein was cloned and sequenced. Although the molecular weight of the protein was previously described in U.S. Pat. No. 5,354,660, its amino acid and nucleic acid sequences were not previously known. In addition, it was determined that several *T. solium* proteins (about nine) co-migrate at this molecular weight, making purification and sequencing of T24 difficult. Cloning of T24 permits rapid and inexpensive recombinant or synthetic production of T24 protein, as compared to the more cumbersome process of isolating T24 from *T solium*. Recombinant or synthetic T24 proteins, alone or in combination with other *T. solium* larval proteins, can be used in immunoassays for the detection of *T. solium* and diagnosis of cysticercosis and neurocysticercosis.

The T24 protein is a membrane protein that migrates at approximately 24 kilodaltons (kDa) using a non-reducing SDS-PAGE. T24 was previously referred to in the literature as GP24; however, it is referred to herein as T24 because the protein extracts into the detergent phase of Triton X-114. A T24 nucleic acid sequence is provided in SEQ ID NO: 1, and the corresponding amino acid sequence in SEQ ID NO: 2. The coding sequence is provided as nucleotides 33-707 of SEQ ID NO: 1. However, this disclosure is not limited to these particular sequences. Variants, fusions, and fragments of SEQ ID NOS: 1 and 2 are encompassed by this disclosure, as long as the protein retains immunogenic activity (or encodes a protein having immunogenic activity), such as amino acids 104-195 of SEQ ID NO: 2 and nucleotides 342-617 of SEQ ID NO: 1.

The disclosed T24 sequences can be used to produce large quantities of highly pure T24 peptide or nucleic acid molecule, and can be used in immunoassays for the detection of *T. solium* and diagnosis of cysticercosis and neurocysticercosis. For example, T24 amino acid sequences can be used to synthesize T24 antigens or T24 antigenic fragments (such as amino acids 104-195 of SEQ ID NO: 2) using known chemical synthesis techniques. In addition, nucleic acid molecules encoding for T24 *T. solium* antigen can be used to recombinantly produce the T24 antigens and antigen fragments, and are also useful as molecular probes or primers for the detection of ribonucleic acid (RNA) and deoxyribonucleic acid (DNA) involved in transcription and translation of *T. solium* peptides. T24 molecular probes and primers provide highly specific and sensitive means to detect and measure *T. solium* larval polypeptides in tissues and cells. Diagnostic and analytical methods and kits are provided for detection and measurement of T24 *T. solium* antibodies, proteins, and nucleic acids in a variety of samples. Such kits can be in any configuration known to those of ordinary skill in the art.

Recombinant or synthetic *T. solium* T24 polypeptides can be used in diagnostic kits to detect the presence and quantity of *T. solium* antibodies, which are diagnostic or prognostic for the occurrence, recurrence or treatment of diseases such as cysticercosis and neurocysticercosis. Methods provided herein include immunoassays that can be used to detect or quantitate the presence of anti-T24 *T. solium* antibodies in a sample, such as human or pig biological fluids or tissue. Such antibodies can also bind to naturally occurring *T. solium* larval antigens, for instance naturally occurring antigens that have been isolated by lentil lectin affinity chromatography. In one example, an immunoassay includes one or more recombinant or synthetic *T. solium* larval peptides or antigenic fragments thereof, such as T24, for the detection of anti-larval antibodies in a sample. An example of such an immunoassay is a rapid immunochromatographic diagnostic test (such as a card test) containing recombinant T24 peptides or antigenic fragments thereof, immunoreactive with anti-T24-*T. solium* antibodies in a sample. Other exemplary methods employ immunoblot and ELISA assays.

This disclosure provides simple, sensitive methods for the diagnosis of cysticercosis or neurocysticercosis, and compositions for use in such methods. For example, methods are provided for detecting *T. solium* cysticercosis, such as diagnosis or monitoring of *T. solium* infection in humans and animals, which is inexpensive, sensitive, and accurate, with little or no cross-reactivity. Stable reagents that can be relatively inexpensively produced are provided that allow for the detection of *T. solium* in a sample. For example, the reagents can include compositions containing recombinant or synthetic *T. solium* larval peptides such as T24. In specific examples, the results produced from the disclosed assays can be interpreted without the use of instrumentation or special temperature conditions.

Other methods allow one to detect the presence of T24 *T. solium* nucleic acids, using nucleic acid hybridization and amplification assays. Nucleic acid probes and primers can be generated based on the nucleic acid sequence shown in SEQ ID NO: 1, or fragments thereof such as nucleotides 342-617 of SEQ ID NO: 1. In one example, probes or primers include at least 10 contiguous nucleotides of SEQ ID NO: 1, for example at least 15, at least 20, at least 25, or even at least 50 contiguous nucleotides of SEQ ID NO: 1.

Compositions and methods for detecting *T. solium* infection and diagnosing diseases related to *T. solium* infection are provided. In some examples, compositions include one or more purified recombinant or synthetic immunogenic, or immunodominant, polypeptides or peptides (or fragments thereof) of the *T. solium* helminth larvae, for instance T24 or antigenic fragments thereof. In some examples, compositions include one or more isolated *T. solium* larvae nucleic acid sequences, such as an isolated T24 nucleic acid sequence. In yet other examples, compositions include one or more antibodies that recognize *T. solium* larvae antigens, such as an anti-T24 antibody.

Recombinant or synthetic *T. solium* T24 peptide can be administered to a subject, alone or in the presence of a pharmaceutical carrier or adjuvant, to generate an immune response against T24 in the subject, thereby protecting the subject against *T. solium* infection and reducing or preventing *T. solium* infection or related disease.

These and other features and advantages of the present disclosure will become apparent after a review of the following detailed description and examples.

BRIEF DESCRIPTION OF THE FIGURES

FIG. 1 is a digital image showing the results from *T. solium* cysts homogenized and extracted with Triton X-114. Lane 1 contains molecular weight markers. Lane 2 is a silver stain of proteins in the aqueous phase. Lane 3 is a silver stain of proteins in the detergent phase. Lane 4 is a western blot of proteins in the detergent phase probed with a cysticercosis positive sera pool. Three membrane proteins are identified, GP50, T42, and T24.

FIGS. 2A and 2B are digital images showing the (A) antibody reactivity of T24 characterized with a panel of cysticercosis positive sera and compared to (B) the antibody reactivity of the western blot GP24. In all cases, the antibody reactivities of the sera with the two antigens were concordant, demonstrating that T24 and GP24 are the same protein. From protein sequencing data, it appears that T42 is a dimer of T24.

SEQUENCE LISTING

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NO: 1 shows a nucleic acid sequence of T24.
SEQ ID NO: 2 shows a protein sequence of T24, encoded by SEQ ID NO: 1.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. As used herein, the singular forms "a" or "an" or "the" include plural references unless the context clearly dictates otherwise. For example, reference to "a T24 protein" includes one or a plurality of such proteins and reference to "the T24 antibody" includes reference to one or more T24 antibodies and equivalents thereof known to those skilled in the art, and so forth.

The term "or" refers to a single element of stated alternative elements or a combination of two or more elements, unless the context clearly indicates otherwise. For example, the phrase "a T24 nucleic acid or a T24 protein" refers to a T24 nucleic acid, a T24 protein, or a combination of a T24 nucleic acid and a T24 protein. As used herein, "comprises" means "includes." Thus, "comprising a T24 peptide," means "including a T24 peptide," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

Animal: Living multi-cellular vertebrate organisms, a category that includes, for example, mammals and birds. The term mammal includes both human and non-human mammals. Similarly, the term "subject" includes both human and veterinary subjects, such as pigs.

Antigen: An agent that can stimulate the production of antibodies or a T-cell response in a subject, such as compositions that are administered to the subject. An antigen reacts with the products of specific humoral or cellular immunity, including those induced by heterologous immunogens. The term "antigen" includes all related antigenic epitopes. Antigenic determinant refers to a region of a protein recognized by an antibody. In one example, an antigen is a T24 antigen that induces an immune response, such as the production of anti-T24 antibodies, in a subject.

cDNA (complementary DNA): A piece of DNA lacking internal, non-coding segments (introns) and regulatory sequences that determine transcription. cDNA can be synthesized by reverse transcription from messenger RNA extracted from cells.

Conservative substitution: One or more amino acid substitutions, such as 2, 3, 5, 10, or 20 substitutions, for amino acid residues having similar biochemical properties. In one example, 2-10 conservative substitutions are included in a peptide, such as 2-5 or 4-9 conservative substitutions in a peptide. Typically, conservative substitutions have little to no impact on the activity of a resulting polypeptide. For example, a conservative substitution is an amino acid substitution in a peptide that does not substantially affect the function of the peptide. In a particular example, a conservative substitution is an amino acid substitution in a T24 peptide, such as a conservative substitution in SEQ ID NO: 2 or a peptide including amino acids 104-195 of SEQ ID NO: 2, which does not significantly decrease immunogenicity of T24.

Methods which can be used to determine the amount of immune response generated by a variant T24 epitope are disclosed. For example, an alanine scan can be used to identify which amino acid residues in a T24 protein can tolerate an amino acid substitution. In one example, the immune response generated is not decreased by more than 25%, for example not more than 20%, for example not more than 10%, when an alanine, or other conservative amino acid (such as those listed below), is substituted for one or more native amino acids, as compared to an immune response generated in the presence of a native T24 protein, such as SEQ ID NO: 2, or amino acids 104-195 of SEQ ID NO: 2.

A peptide can be produced to contain one or more conservative substitutions by manipulating the nucleotide sequence that encodes that polypeptide using, for example, standard procedures such as site-directed mutagenesis or PCR. Alternatively, a peptide can be produced to contain one or more conservative substitutions by using standard peptide synthesis methods.

Substitutional variants are those in which at least one residue in the amino acid sequence has been removed and a different residue inserted in its place. Examples of amino acids which can be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val. Further information about conservative substitutions can be found in, among other locations in, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988) and in standard textbooks of genetics and molecular biology.

Deletion: The removal of a sequence, such as a nucleic acid or amino acid sequence, the regions on either side being joined together.

Degenerate variant: A polynucleotide encoding a peptide, such as T24, that includes a sequence that is degenerate as a result of the genetic code. There are 20 natural amino acids, most of which are specified by more than one codon. Therefore, all degenerate nucleotide sequences are included as long as the amino acid sequence of the peptide, such as T24, encoded by the nucleotide sequence is unchanged.

Detection: The ability to quantitatively or qualitatively determine the presence of a biomolecule under investigation. In one example the biomolecule is one or more *T. solium* larval proteins, such as T24, GP50, GP39-42, GP21, GP18, GP14 or GP13.

Enhance: To improve the quality, amount, or strength of something. In one example, a therapy enhances the immune system if the immune system is more effective at reducing infection by *T. solium* or reducing the development of one or more symptoms associated with cysticercosis or neurocysticercosis. In a particular example, a T24 epitope reduces a subject's susceptibility to a *T. solium* infection. Such reduction can be measured using any bioassay known in the art, for example, an ELISA assay.

Functionally Equivalent: A functionally equivalent molecule is a molecule that is altered from the original molecule, but retains essentially the same functions as the non-altered molecule. In one example, a functionally equivalent protein includes one or more amino acid alterations and retains a function of the unaltered protein, such as it specifically binds an antibody that binds an unaltered form of the eptiope, or wherein the epitope with one or more sequence alterations retains the ability to induce an immune response in a subject.

Examples of sequence alterations include, but are not limited to, conservative substitutions, deletions, mutations, frameshifts, and insertions. In one example, a given polypeptide binds an antibody, and a functional equivalent is a polypeptide that binds the same antibody. Thus a functional equivalent includes peptides which have the same binding specificity as a polypeptide, and which can be used as a reagent in place of the polypeptide (such as in a diagnostic assay or vaccine). In one example a functional equivalent includes a polypeptide wherein the binding sequence is discontinuous, wherein the antibody binds a linear epitope. Thus, if the peptide sequence is MALSCGGDFL (amino acids 1-10 of SEQ ID NO: 2) a functional equivalent includes discontinuous epitopes, which may can appear as follows (=any number of intervening amino acids): NH2--MALSCGGDF**L-COOH. This polypeptide is functionally equivalent to SEQ ID NO: 2 if the three dimensional structure of the polypeptide is such that it can bind a monoclonal antibody that binds SEQ ID NO: 2, or if it retains the ability to be stimulate an immune response in a subject.

Immune response: A change in immunity, for example, a response of a cell of the immune system, such as a B cell, T cell, or monocyte, to a stimulus. In one example, the response is specific for a particular antigen (an "antigen-specific response"), such as a response to a T24 peptide antigen. In one example, an immune response is a T cell response, such as a $CD4^+$ response or a $CD8^+$ response. In another example, the response is a B cell response, and results in the production of specific antibodies, for example antibodies that recognize T24. In a particular example, an increased or enhanced immune response is an increase in the ability of a subject to fight off a disease, such as cysticerosis or neurocysticerosis.

Immune stimulatory composition: A pharmaceutical composition which includes a T24 protein (or a variant, fusion, or fragment thereof, such as amino acids 104-195 of SEQ ID NO: 2), which when administered to a subject, results in the subject producing antibodies against a T24 protein. The subject's response results in treatment of the subject suffering from cysticerosis or neurocysticerosis. Such compositions can contain other molecules, for example a pharmaceutically acceptable carrier or an adjuvant.

Isolated: An "isolated" biological component (such as a nucleic acid molecule or protein) has been substantially separated, produced apart from, or purified away from other biological components in the cell of the organism in which the component naturally occurs, such as other chromosomal and extrachromosomal DNA and RNA, and proteins. Nucleic acid molecules and proteins which have been "isolated" include nucleic acid molecules and proteins purified by standard purification methods. The term also includes nucleic acid molecules and proteins prepared by recombinant expression in a host cell as well as chemically synthesized nucleic acid molecules and peptides.

Modulating an Immune Response: The ability to increase or decrease an immune response in a subject, such as the ability to stimulate a CTL immune response, by a desired amount. Agents that modulate an immune response include, but are not limited to: T24 polypeptides (such as SEQ ID NO: 2 as well as fragments, variants, fusions, and polymorphisms thereof, for example amino acids 104-195 of SEQ ID NO: 2), T24 nucleic acid molecules encoding T24 peptides (such as SEQ ID NO: 1 as well as fragments, variants, fusions, and polymorphisms thereof, for example nucleotides 342-617 of SEQ ID NO: 1), T24 specific binding agents, T24 antisense molecules, and immunoreactive sensitized T cells sensitized with T24.

Nucleic acid molecule: A deoxyribonucleotide or ribonucleotide polymer in either single or double stranded form. Includes analogues of natural nucleotides that hybridize to nucleic acids in a manner similar to naturally occurring nucleotides.

Oligonucleotide: A linear polynucleotide (such as DNA or RNA) sequence of at least 9 nucleotides, for example at least 10, at least 12, at least 15, at least 18, at least 24, at least 25, at least 27, at least 30, at least 50, at least 100 or even at least 200 nucleotides long. In a particular example, an oligonucleotide includes at least 9 contiguous nucleotides of SEQ ID NO: 1, such as at least 12, at least 15, at least 18, at least 24, at least 25, at least 27, at least 30, at least 50, at least 100 or even at least 200 contiguous nucleotides of SEQ ID NO: 1.

ORF (open reading frame): A series of nucleotide triplets (codons) coding for amino acids without any termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Peptide Modifications: One or more alterations to a native peptide. The present disclosure includes T24 proteins, as well as analogues (non-peptide organic molecules), derivatives (chemically functionalized peptide molecules obtained starting with the disclosed peptide sequences) and variants (homologs) of T24 that can generate an immune response. T24 peptides having one or more modifications can be utilized in the methods described herein. The peptides disclosed herein include a sequence of amino acids, which may be either L- or D-amino acids, naturally occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into a T24 peptide to select and provide conformational constraints to the structure that result in enhanced stability.

Peptidomimetic and organomimetic embodiments are also within the scope of the present disclosure, whereby the three-dimensional arrangement of the chemical constituents of such peptido- and organomimetics mimic the three-dimensional arrangement of the peptide backbone and component amino acid side chains, resulting in such peptido- and organomimetics of the proteins of this disclosure having measurable or enhanced ability to bind an antibody. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacolo*, Munson (ed.) 1995, Ch. 102, for descriptions of techniques used in CADD. Also included within the scope of the disclosure are mimetics prepared using such techniques. In one example, a mimetic mimics the immune response generated by a T24 peptide or antigenic fragment thereof.

Pharmaceutical agent or drug: A chemical compound or composition capable of inducing a desired therapeutic or prophylactic effect when properly administered to a subject.

Pharmaceutically acceptable carriers: The pharmaceutically acceptable carriers useful herein are conventional. *Remington's Pharmaceutical Sciences*, by E. W. Martin, Mack Publishing Co., Easton, Pa., 15th Edition (1975), describes compositions and formulations suitable for pharmaceutical delivery of the peptides and nucleic acids herein disclosed.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (such as a powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A linear nucleic acid sequence of at least 3 nucleotides. Therefore, a polynucleotide includes molecules which are at least 15, at least 20, at least 24, at least 27, at least 30, at least 50, at least 100, at least 200, at least 500, at least 1000, or at least 5000 nucleotides in length, and also nucleotides as long as a full length cDNA. A T24 polynucleotide encodes a T24 peptide.

In a particular example, a polynucleotide includes at least 9 contiguous nucleotides of SEQ ID NO: 1, such as at least 12, at least 20, at least 30, at least 50, at least 100, at least 200, at least 250, at least 300, at least 400, at least 600 or even at least 800 contiguous nucleotides of SEQ ID NO: 1.

Polypeptide: Any chain of amino acids at least six amino acids in length, such as at least 10 amino acids, at least 14 amino acids, at least 20 amino acids, at least 92 amino acids, even at least 100 amino acids regardless of post-translational modification (such as glycosylation or phosphorylation). In one example, a polypeptide is a T24 peptide, such as SEQ ID NO: 2 or fragments thereof such as amino acids 104-195 of SEQ ID NO: 2.

In a particular example, a polynucleotide includes at least 10 contiguous amino acids of SEQ ID NO: 2, such as at least 12, at least 20, at least 30, at least 50, at least 75, at least 90, at least 92, at least 100, at least 150, at least 200 or even at least 210 contiguous amino acids of SEQ ID NO: 2.

Preventing or treating a disease: "Preventing" a disease refers to inhibiting the full development of a disease, for example preventing development or progression of cysticerosis or neurocysticerosis. "Treatment" refers to a therapeutic intervention that ameliorates a sign or symptom of a disease or pathological condition related to cysticerosis or neurocysticerosis, such as inflammation, fever, muscle pains, eosinophilia, meningoencephalitis, epileptic seizures, dementia or other neurologic or psychiatric manifestations, or acute intracranial hypertension.

Probes and primers: Nucleic acid probes and primers can readily be prepared based on the T24 sequences provided herein.

A probe includes an isolated nucleic acid attached to a detectable label or reporter molecule. Typical labels include, but are not limited to, radioactive isotopes, ligands, fluorophores, chemiluminescent agents, and enzymes. Methods for labeling and guidance in the choice of labels appropriate for various purposes are discussed, for example, in Sambrook et al, *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

Primers are short nucleic acids, such as DNA oligonucleotides about at least 12 nucleotides in length. Primers can be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example by PCR or other nucleic-acid amplification methods known in the art. A "primer pair" refers to two primers, one having a forward designation and the other having a reverse designation (relative to their respective orientations on a double-stranded DNA molecule that includes a sense and antisense sequence), such that under amplification conditions the forward primer anneals to and primes amplification of the sense sequence and the reverse primer anneals to and primes amplification of the antisense sequence.

Methods for preparing and using probes and primers are described, for example, in Sambrook et al. (*Molecular Cloning: A Laboratory Manual*, Cold Spring Harbor Laboratory Press, 1989), Ausubel et al., 1987, and Innis et al., *PCR Protocols, A Guide to Methods and Applications,* 1990, Innis et al. (eds.), 21-27, Academic Press, Inc., San Diego, Calif. PCR primer pairs can be derived from a known sequence, for example, by using computer programs intended for that purpose such as Primer (Version 0.5, © 1991, Whitehead Institute for Biomedical Research, Cambridge, Mass.).

One of skill in the art will appreciate that the specificity of a particular probe or primer increases with its length. Thus, for example, a primer consisting of 20 consecutive nucleotides of SEQ ID NO: 1 will anneal to a target sequence, such as a T24 homolog contained within a genomic DNA library, with a higher specificity than a corresponding primer of only 15 nucleotides. Thus, to obtain greater specificity, probes and primers can be selected that include at least 25, at least 30, at least 35, at least 40, at least 50 or more consecutive nucleotides of SEQ ID NO: 1.

In addition, T24 cDNA and gene sequences can be apportioned into halves or quarters based on sequence length, and the isolated nucleic acid molecules can be derived from the first or second halves of the molecules, or any of the four quarters. In particular, the DNA sequences may code for a unique portion of T24, such as an immunogenic fragment of T24, such as amino acids 104-195 of SEQ ID NO: 2.

Promoter: An array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Both constitutive and inducible promoters are included (Bitter et al., Meth. Enzymol. 153:516-44, 1987). Exemplary promoters are provided below.

Purified: The term purified does not require absolute purity; rather, it is intended as a relative term. Thus, for example, a purified peptide preparation is one in which the peptide or protein is more enriched than the peptide or protein is in its generative environment, for instance within a cell or in a biochemical reaction chamber. Therefore, a purified peptide is substantially separated from cellular components (such as nucleic acids, lipids, carbohydrates, and other polypeptides) that can accompany it. In another example, a purified peptide preparation is one in which the peptide is substantially-free from contaminants, such as those that can be present following chemical synthesis of the peptide.

A preparation of substantially pure peptide, such as T24 peptide, can be purified such that the desired peptide represents at least 50% by weight of a sample. In certain examples, a substantially pure peptide represents at least 60%, at least 70%, at least 80%, at least 85%, at least 90%, at least 95%, or at least 98% or more by weight of the total peptide content of the preparation.

Examples of methods that can be used to purify a peptide, include, but are not limited to the methods disclosed in Sambrook et al. (*Molecular Cloning: A Laboratory Manual*, Cold Spring Harbor, N.Y., 1989, Ch. 17). Protein purity can be determined by, for example, polyacrylamide gel electrophoresis of a protein sample, followed by visualization of a single polypeptide band upon staining the polyacrylamide gel; high-pressure liquid chromatography; sequencing; or other conventional methods.

Recombinant: A recombinant nucleic acid is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acids, such as by genetic engineering techniques. Similarly, a recombinant protein is one encoded for by a recombinant nucleic acid molecule, or a protein produced by other synthetic methods using technology known in the art.

Sample: Material obtained from a subject. In some examples, the sample is a cell(s) obtained from a subject that includes genomic DNA, cDNA, RNA, or protein. Exemplary samples include, but are not limited to: peripheral blood, urine, saliva, tissue biopsy, surgical specimen, fine needle aspriates, amniocentesis samples and autopsy material.

Sequence identity: The similarity between nucleic acid or amino acid sequences is expressed in terms of the similarity between the sequences. Sequence identity is frequently measured in terms of percentage identity (or similarity or homology); the higher the percentage, the more similar the two sequences are. Homologs or variants of a protein or nucleic acid molecule disclosed herein, such as SEQ ID NOS: 1-2, will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-44, 1988; Higgins and Sharp, *CABIOS* 5:151-3, 1989; Corpet et al., *Nucl. Acids Res.* 16:10881-90, 1988; Pearson and Lipman, *Proc. Natl. Acad. Sci. U.S.A.* 85:2444, 1988; and Altschul et al., *Nature Genet.* 6:119-29, 1994.

The NCBI Basic Local Alignment Search Tool (BLAST™) (Altschul et al., *J. Mol. Biol.* 215:403-10, 1990) is available from several sources, including the National Center for Biotechnology Information (NCBI, Bethesda, Md.) and on the Internet, for use in connection with the sequence analysis programs blastp, blastn, blastx, tblastn and tblastx.

Variants of a peptide, such as a T24 peptide shown in SEQ ID NO: 2, or amino acids 104-195 of SEQ ID NO: 2 are typically characterized by possession of at least 85% sequence identity counted over the full length alignment with the amino acid sequence shown in SEQ ID NO: 2 or amino acids 104-195 of SEQ ID NO: 2 using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment is performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 90%, at least 95%, at least 98%, or even at least 99% sequence identity. When less than the entire sequence is being compared for sequence identity, homologs and variants will typically possess at least 85% sequence identity over short windows of 10-20 amino acids, and may possess sequence identities of at least 90%, at least 95%, or at least 98% depending on their similarity to the reference sequence. Methods for determining sequence identity over such short windows are described at the website that is maintained by the National Center for Biotechnology Information in Bethesda, Md. One of skill in the art will appreciate that these sequence identity ranges are provided for guidance only; it is entirely possible that strongly significant homologs could be obtained that fall outside of the ranges provided.

Similar methods can be used to determine the sequence identity between two or more nucleic acid molecules. To compare two nucleic acid sequences, the BLASTN options can be set as follows: —i is set to a file containing the first nucleic acid sequence to be compared (such as C:\seq1.txt); —j is set to a file containing the second nucleic acid sequence to be compared (such as C:\seq2.txt); —p is set to blastn; —o is set to any desired file name (such as C:\output.txt); —q is set to −1; —r is set to 2; and all other options are left at their default setting. For example, the following command can be used to generate an output file containing a comparison between two sequences: C:\B12seq-i c:seq1.txt-j c:\seq2.txt-p blastn-o c:\output.txt-q-1-r 2.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (15÷20*100=75).

```
                              1                   20
   Target Sequence:     ATGGGTCTCTCATGCGGCGG
                        | || ||| |||| |||| |
   Identified Sequence: ACGGTTCTATCATCCGGCAG
```

The T24 nucleic acid molecules disclosed herein, such as SEQ ID NO: 1, include nucleic acids having at least 85%, at least 90%, at least 95%, at least 98%, or at least 99% identical to the nucleotide sequence of SEQ ID NO: 1 or nucleotides 342-617 of SEQ ID NO: 1. In particular examples, a nucleic acid molecule is substantially similar to the nucleotide sequence of SEQ ID NO: 1 or nucleotides 342-617 of SEQ ID NO: 1. A first nucleic acid molecule is "substantially similar" to a second nucleic acid molecule if, when the first nucleic acid molecule is optimally aligned (with appropriate nucleotide deletions or gap insertions) with the second nucleic acid molecule (or its complementary strand) and there is nucleotide sequence identity of at least about 90%, for example at least about 95%, at least 98% or at least 99% identity. An alternative indication that two nucleic acid molecules are closely related is that the two molecules hybridize to each other under stringent conditions.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Specific binding agent: An agent that binds substantially only to a defined target. Thus a T24 specific binding agent is an agent that binds substantially to a T24 polypeptide. In one example, the specific binding agent is a monoclonal or polyclonal antibody. Methods for producing antibodies are provided below.

Shorter fragments of antibodies can also serve as specific binding agents. For instance, Fabs, Fvs, and single-chain Fvs (SCFvs) that bind to a specified protein are specific binding agents. These antibody fragments include: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine. For example, construction of Fab expression libraries permits the rapid and easy identification of monoclonal Fab fragments with the desired specificity for a T24 protein.

T24 cDNA: As used herein, a T24 cDNA includes T24 cDNAs from any organism, such as *T. solium*. In one example, a T24 cDNA includes SEQ ID NO: 1, as well as fragments, fusions, and variants thereof. In some examples, such fragments, variants, or fusions encode a T24 protein that can stimulate an immune response, encode a T24 protein that can immunoreact with T24 antibodies, or combinations thereof. Exemplary fragments include nucleotides 33-710 of SEQ ID NO: 1 or nucleotides 342-617 of SEQ ID NO: 1. T24 cDNA can be derived by reverse transcription from the mRNA encoded by a T24 gene and lacks internal non-coding segments and transcription regulatory sequences present in a T24 gene.

T24 gene: A gene that encodes a T24 protein from any organism, such as *T. solium*. A T24 gene includes the various sequence polymorphisms and allelic variants that exist within and between species.

T24 peptide: A protein encoded by a T24 gene or cDNA from any organism, such as *T. solium*. The immunogenic T24 larval *T. solium* membrane protein migrates at approximately 24 kDa on a non-reducing SDS-PAGE, and extracts into the detergent phase of Triton X-114. A T24 protein includes a full-length transcript, such as SEQ ID NO: 2, as well as fragments, fusions, and variants of SEQ ID NO: 2 that retain the ability to stimulate an immune response, to immunoreact with T24 antibodies, or combinations thereof. An exemplary fragment includes amino acids 104-195 of SEQ ID NO: 2.

Therapeutically active molecule: An agent, such as a T24 protein or nucleic acid molecule, for example SEQ ID NOS: 1-2 (or variants, fusions, or fragments thereof), or T24 antibody, that can induce an immune response, as measured by clinical response (for example increase in a population of immune cells, or measurable reduction in *T. solium* infection). Therapeutically active agents can also include organic or other chemical compounds that mimic the effects of a T24 peptide, T24 nucleic acid molecule, or T24 antibody.

Therapeutically Effective Amount: The preparations disclosed herein are administered in therapeutically effective amounts. An effective amount is that amount of a pharmaceutical preparation that alone, or together with further doses, stimulates the desired response.

In one example, a desired response is stimulation of a CTL response to T24, resulting in halting or slowing the progression of, or inducing a regression of a pathological condition or which is capable of relieving signs or symptoms caused by the condition. One example of a therapeutic effect is regression of one or more symptoms associated with cysticercosis or neurocysticercosis. Treatment can involve slowing the progression of the disease temporarily, and can also include halting or reversing the progression of the disease permanently.

The therapeutically effective amount also includes a quantity of T24 protein, nucleic acid molecule (such as SEQ ID NOS: 1-2, or variants, fusions or fragments thereof), or T24 antibody, sufficient to achieve a desired effect in a subject being treated. For instance, this can be the amount necessary to improve signs or symptoms a disease such as cysticercosis or neurocysticercosis, for example by decreasing one or more of inflammation, fever, muscle pains, eosinophilia, meningoencephalitis, epileptic seizures, dementia or other neurologic or psychiatric manifestations, and acute intracranial hypertension in a subject.

An effective amount of T24 protein can be administered in a single dose, or in several doses, for example daily, during a course of treatment. However, the effective amount can depend on the source applied (for example T24 peptide isolated from a cellular extract versus a chemically synthesized and purified T24 peptide, or a variant or fragment that may not retain full T24 activity), the subject being treated, the severity and type of the condition being treated, and the manner of administration. For example, a therapeutically effective amount of T24 protein, can vary from about 0.01 mg/kg body weight to about 1 g/kg body weight, such as about 1 mg per subject.

The methods disclosed herein have equal application in medical and veterinary settings. Therefore, the general term "subject being treated" is understood to include all animals (such as humans and pigs) that require an immune response against T24, for example to reduce symptoms associated with cysticercosis or neurocysticercosis.

Transduced, transformed and transfected: A transduced, transformed, or transfected cell is a cell into which an exogenous nucleic acid molecule has been introduced, and wherein the nucleic acid molecule becomes stably replicated by the cell, either by incorporation of the nucleic acid molecule into the cellular genome, or by episomal replication. A virus or vector "transduces" or "transfects" a cell when it transfers nucleic acid molecules into the cell. These terms encompasses all techniques by which a nucleic acid molecule can be introduced into such a cell, including, but not limited to, transfection with viral vectors, transformation with plasmid vectors, and introduction of naked DNA by electroporation, lipofection, and particle gun acceleration.

Transgene: An exogenous nucleic acid sequence, for example, a nucleic acid sequence supplied by a vector. In one example, a transgene encodes a T24 peptide.

Variants or fragments or fusion molecules: The disclosed T24 proteins and nucleic acid molecules include variants, fragments, and fusions thereof. DNA sequences which encode for T24 or fusion, fragment, or variant thereof (for example a fragment or variant having at least 85%, at least 90%, or at least 95% sequence identity to nucleotides 33-710 of SEQ ID NO: 1 or nucleotides 342-617 of SEQ ID NO: 1) can be engineered to allow a T24 protein to be expressed in a host cells, such as a bacteria, insect, mammalian, yeast, or plant cell. To obtain expression, the DNA sequence can be altered and operably linked to other regulatory sequences. The final product, which contains the regulatory sequences and the therapeutic protein, is referred to as a vector. This vector can be introduced into a host cell. Once inside the cell, the vector allows the protein to be produced.

A fusion protein including T24 (or variants, polymorphisms, mutants, or fragments thereof, such as amino acids 104-195 of SEQ ID NO: 2) linked to other amino acid sequences that do not inhibit the desired activity of the protein, for example the ability to stimulate an immune response, interact with a T24 antibody, or both. In one example, the other amino acid sequences are no more than 8, 9, 10, 12, 15, 20, 30, or 50 amino acid residues in length.

One of ordinary skill in the art will appreciate that the DNA can be altered in numerous ways without affecting the biological activity of the encoded protein. For example, PCR can be used to produce variations in the DNA sequence which encodes a protein. Such variants can be variants optimized for codon preference in a host cell used to express the protein, or other sequence changes that facilitate expression.

Vector: A nucleic acid molecule as introduced into a host cell, thereby producing a transformed host cell. A vector can include nucleic acid sequences that permit it to replicate in the host cell, such as an origin of replication. A vector can also include one or more therapeutic genes or selectable marker genes and other genetic elements known in the art. A vector can transduce, transform or infect a cell, thereby causing the cell to express nucleic acid molecules or proteins other than those native to the cell. A vector optionally includes materials to aid in achieving entry of the nucleic acid into the cell, such as a viral particle, liposome, protein coating or the like. In one example, a vector is a viral vector. Viral vectors include, but are not limited to, retroviral and adenoviral vectors.

*Taenia solium* T24 Polypeptides

Previously, several immunogenic *T. solium* peptides were identified by molecular weight (see U.S. Pat. No. 5,354,660). However, until now the T24 protein and nucleic sequences had not been identified. Purification and cloning of T24 was difficult because at least nine proteins, including T24, co-migrate at 24 kDa on a non-reducing SDS-PAGE. Therefore, the T24 present in the band that migrates at 24 kDa on a non-reducing SDS-PAGE is not substantially pure. It is likely that these previous preparations of T24 were only about 30% pure by weight, due to the contaminating proteins that co-migrate at 24 kDa.

Nucleic acid and protein sequences of *T. solium* T24 are disclosed. However, the disclosure is not limited to these particular sequences, as the disclosed T24 sequences can be subject to various changes, such as insertions, deletions, and substitutions. Such variations can provide for certain advantages, for example to increase biological activity.

In one example, substantially purified T24 protein is provided, for example a T24 protein preparation that is at least 60% pure by weight, such as at least 80%, at least 90%, at least 95%, or even at least 98% pure by weight. A native T24 protein sequence is shown in SEQ ID NO: 2. However, this disclosure includes T24 protein variants, fusions, and fragments that can elicit or stimulate an immune response, react with a T24 antibody (such as those found in subjects having a *T. solium* infection), or combinations thereof. Variant sequences can contain a single insertion, a single deletion, a single substitution, multiple insertions, multiple deletions, multiple substitutions, or any combination thereof (such as a single deletion together with multiple insertions). One particular example of a T24 fragment includes amino acids 104-195 of SEQ ID NO: 2. In one example, a T-cell that recognizes a T24 peptide can also recognize a variant of T24. In another or additional example, such variant immunogenic peptide sequences can stimulate propagation of an immune cell (such as a T-cell). The disclosed T24 peptides are immunogenic, and can be used to elicit an immune response in a subject, such as those subjects having a *T. solium* infection.

Minor modifications of the primary amino acid sequence of T24 can result in peptides which have substantially equivalent activity as compared to the unmodified counterpart T24 peptide described herein. Such modifications may be deliberate, as by site-directed mutagenesis, or can be spontaneous. All of the peptides produced by these modifications are included herein as long as an activity of variant peptide, such as the ability to induce an immune response, still exists. In one example, such variants have at least 90% identity, such as at least 95% identity, to the disclosed sequences. Particular examples of variants include those having one or more, two or more, such as 2-10 conservative amino acid substitutions. In one example, a variant includes a single amino acid substitution, such as a single conservative amino acid substitution.

Purified T24 peptides can be at least 6 amino acids in length, such as at least 8, at least 9, at least 10, at least 11, at least 12, at least 15, at least 20, at least 30, at least 50, at least 90, at least 92, or even at least 100 amino acids in length. One skilled in the art will understand that fusion proteins including a T24 peptide can be even longer.

Certain compositions provided herein contain recombinant or synthetic *T. solium* T24 peptides that are immunoreactive with *T. solium* antibodies. *T. solium* antibodies are, in certain examples, derived from the sera, saliva, cerebrospinal fluid or urine of patients infected with *T. solium. Alternatively, antibodies are produced in an experimental animal by administration of T*24 peptide or an antigenic fragment thereof, such as amino acids 104-195 of SEQ ID NO: 2. In specific examples, the recombinant or synthetic T24 peptides correspond to naturally occurring proteins having a molecular weight of approximately 24 kDa. In certain instances, T24 peptides are encoded by a sequence that includes SEQ ID NO: 1, or variants, fragments, or fusions thereof, such as nucleotides 33-710 of SEQ ID NO: 1 or nucleotides 342-617 of SEQ ID NO: 1.

The disclosed immunoreactive T24 polypeptides include T24 peptide analogs, which include antigenic peptides containing amino acid sequences differing from those shown in SEQ ID NO: 2 (or amino acids 104-195 of SEQ ID NO: 2) by one or more amino acid substitutions at any position, or which have other molecules attached to amino acid functional groups within the sequence. Also disclosed are immunoreactive fragments (antigenic fragments) of T24 having substantially the same antigenicity of T24 peptide, or the functional equivalent thereof. In certain examples, T24 antigenic fragments contain amino acid sequences that are homologous or substantially homologous to T24. In a specific example, a T24 antigenic fragment includes amino acid sequences that are homologous or substantially homologous to SEQ ID NO: 2.

The *T. solium* T24 peptides described herein have a variety of uses. For example T24 peptides or antigenic fragments thereof can be used as reagents in immunoassays for the detection of *T. solium* antibodies as described below. Furthermore, *T. solium* polypeptides can be employed in affinity columns for isolating *T. solium* antibodies. Also, T24 peptides that bind to *T. solium* T24-antibodies with high specificity and avidity can be labeled with a label or reporter group and employed for visualization and quantitation in the assays described herein using detection techniques such as autoradiographic and membrane binding techniques. Such applications provide important diagnostic and research tools. In addition, the disclosed T24 peptides can be used to stimulate an immune response, for example to prevent or treat cysticercosis or neurocysticercosis.

Production of Synthetic and Recombinant T24 *T. solium* Peptides

The T24 sequences provided herein can be used to produce T24 peptides and T24 antigenic fragments using recombinant or synthetic methods known to those skilled in the art.
Synthetic Methods A synthetic T24 peptide refers to a T24 polypeptide formed in vitro by joining amino acids in a particular order, for example using organic chemistry to form the peptide bonds. Methods for preparing synthetic polypeptides are known in the art. For example, T24 peptides can be synthesized using solid phase techniques, cleaved from the resin, and purified by preparative high performance liquid chromatography (for example see Creighton, 1983, Proteins Structures And Molecular Principles, W. H. Freeman and Co., N.Y. pp. 50-60; Barany and Merrifield, *Solid-Phase Peptide Synthesis, in The Peptides: Analysis, Synthesis*, Biology (Gross and Meienhofer (eds.), Academic Press, N.Y., vol. 2, pp. 3-284 (1980)); Merrifield, et al., *J. Am. Chem. Soc.* 85:2149-56 (1963); Stewart, et al., *Solid Phase Peptide Synthesis* (2nd ed., Pierce Chem. Co., Rockford, Ill. (1984)); S. B. H. Kent, Biomedical Polymers, eds. Goldberg and Nakajima, Academic Press, New York, pp. 213-242, 1980; Mitchell et al., J. Org. Chem., 43:2845-52, 1978; Tam et al., *Tet. Letters,* 4033-6, 1979; Mojsov et al., *J. Org. Chem.,* 45:555-60, 1980; Tam et al., *Tet Letters,* 2851-4, 1981; and Kent et al., Proceedings of the IV International Symposium on Methods of Protein Sequence Analysis, (Brookhaven Press, Brookhaven, N.Y., 1981); all of which are hereby incorporated by reference). The composition of the synthetic peptides can be confirmed by amino acid or sequence analysis (such as Edman degradation; see Creighton, 1983, Proteins, Structures and Molecular Principles, W. H. Freeman and Co., N.Y., pp. 34-49). Smaller peptides can be joined to form larger polypeptides using chemical ligation (Wilken and Kent, *Current Opinion in Biotechnology* 4:412-26, 1998).

Briefly, solid phase synthesis is started from the C-terminal end of a T24 peptide by coupling a protected amino acid via its carboxyl group to a suitable solid support. The solid support used is not a critical feature, but ideally is capable of binding to the carboxyl group while remaining substantially inert to the reagents utilized in the peptide synthesis procedure. For example, a starting material can be prepared by attaching an amino-protected amino acid via a benzyl ester linkage to a chloromethylated resin or a hydroxymethyl resin or via an amide bond to a benzhydrylamine (BHA) resin or p-methylbenzhydrylamine (MBHA) resin. Exemplary materials suitable for use as solid supports are well known and include: halomethyl resins, such as chloromethyl resin or bromomethyl resin; hydroxymethyl resins; phenol resins, such as 4-(a-[2,4-dimethoxyphenyl]-Fmoc-aminomethyl) phenoxy resin; tert-alkyloxycarbonyl-hydrazidated resins, and the like. Such resins are commercially available and their methods of preparation are known.

The acid form of T24 peptides can be prepared using a solid phase peptide synthesis method using a benzyl ester resin as a solid support. The corresponding amides can be produced by using benzhydrylamine or methylbenz-hydrylamine resin as the solid support. When BHA or MBHA resin is used, treatment with anhydrous hydrofluoric acid to cleave the peptide from the solid support produces a peptide having a terminal amide group.

The α-amino group of each amino acid used in the synthesis can be protected during the coupling reaction to prevent side reactions involving the reactive α-amino function. Certain amino acids also contain reactive side-chain functional groups (such as sulfhydryl, amino, carboxyl, hydroxyl, etc.) that ideally are protected with appropriate protecting groups to prevent chemical reactions from occurring at those sites during peptide synthesis. Protecting groups are well known.

Ideally, an α-amino protecting group will render the α-amino function inert during the coupling reaction, will be readily removable after coupling under conditions that will not remove side chain protecting groups, will not alter the structure of the peptide fragment, and will prevent racemization upon activation immediately prior to coupling. Similarly, side-chain protecting groups are chosen to render the side chain functional group inert during the synthesis, are stable under the conditions used to remove the α-amino protecting group, and are removable after completion of the peptide synthesis under conditions that will not alter the structure of the peptide.

Coupling of the amino acids can be accomplished by a variety of methods. Typical approaches involve either the conversion of the amino acid to a derivative that will render the carboxyl group more susceptible to reaction with the free N-terminal amino group of the peptide fragment, or use of a suitable coupling agent such as, for example, N,N'-dicyclohexylcarbodiimide (DCC) or N,N'-diisopropylcarbodiimide (DIPCDI). Hydroxybenzotriazole (HOBt) can be employed as a catalyst in these coupling reactions. Appropriate synthesis chemistries are disclosed in The Peptides: Analysis, Structure, Biology, Vol. 1: Methods of Peptide Bond Formation (Gross and Meienhofer (eds.), Academic Press, N.Y., 1979); and Izumiya, et al., Synthesis of Peptides (Maruzen Publishing Co., Ltd., 1975).

Generally, synthesis of the peptide is commenced by first coupling the C-terminal amino acid, which is protected at the N-amino position by a protecting group such as fluorenylmethyloxycarbonyl (Fmoc), to a solid support. Prior to coupling of Fmoc-Asn, the Fmoc residue has to be removed from the polymer. Fmoc-Asn can, for example, be coupled to the 4-(a-[2,4-dimethoxyphenyl]-Fmoc-amino-methyl)phenoxy resin using N,N'-dicyclohexylcarbodiimide (DCC) and hydroxybenzotriazole (HOBt) at about 25° C. for about two hours with stirring. Following the coupling of the Fmoc-protected amino acid to the resin support, the α-amino protecting group is removed using 20% piperidine in DMF at room temperature.

After removal of the α-amino protecting group, the remaining Fmoc-protected amino acids are coupled stepwise in the desired order. Appropriately protected amino acids are commercially available from a number of suppliers (for example Novartis (Switzerland) or Bachem (CA)). As an alternative to the stepwise addition of individual amino acids, appropriately protected peptide fragments consisting of more than one amino acid can also be coupled to the "growing" peptide. Selection of an appropriate coupling reagent, as explained above, is well known to those of skill in the art. If a T24 immunogenic peptide is relatively short in length, this latter approach (the segment condensation method) is not the most efficient method of peptide synthesis.

Each protected amino acid or amino acid sequence is introduced into the solid phase reactor in excess and the coupling is carried out in a medium of dimethylformamide (DMF), methylene chloride ($CH_2Cl_2$), or mixtures thereof. If coupling is incomplete, the coupling reaction can be repeated before deprotection of the N-amino group and addition of the next amino acid. Coupling efficiency can be monitored, for example using the ninhydrin reaction. Peptide synthesis reactions can be performed automatically using a number of commercially available peptide synthesizers (such as Biosearch 9500, Biosearch, San Raphael, Calif.).

The peptide can be cleaved and the protecting groups removed by stirring the insoluble carrier or solid support in anhydrous, liquid hydrogen fluoride (HF) in the presence of anisole and dimethylsulfide at about 0° C. for about 20 to 90 minutes, in particular examples about 60 minutes; by bubbling hydrogen bromide (HBr) continuously through a 1 mg/10 mL suspension of the resin in trifluoroacetic acid (TFA) for 60 to 360 minutes at about room temperature, depending on the protecting groups selected; or by incubating the solid support inside the reaction column used for the solid phase synthesis with 90% trifluoroacetic acid, 5% water and 5% triethylsilane for about 30 to 60 minutes. Other deprotection methods can also be used.

The synthesized T24 peptides can be isolated and purified from the reaction mixture by means of peptide purification known to those of skill in the art. For example, the peptides can be purified using chromatographic procedures such as reverse phase HPLC, gel permeation, ion exchange, size exclusion, affinity, partition, or countercurrent distribution.

Recombinant Methods

Recombinant T24 proteins can be produced by known methods. For example, a T24 nucleotide sequence can be inserted into a vector, such as a plasmid, and recombinantly expressed in a host cell to produce recombinant T24 peptides.

Briefly, a cloning vector, such as a plasmid or phage DNA is cleaved with one or more restriction enzymes, and a T24 nucleic acid sequence encoding a T24 protein (or variant or fragment thereof) is inserted into the cleavage site and ligated. The cloning vector is introduced into a host cell to produce the T24 peptide encoded by the nucleic acid. Suitable hosts include bacterial hosts, such as *Escherichia coli* and *Bacillus subtilis*, as well as yeast, plant, insect, and mammalian cell lines, and other cell cultures. Insect cell expression can be used to generate a large amount of protein for use in a diagnostic assay, and can be used when a protein includes disulfide bonds (such as T24). Exemplary insect cell lines include the *D. melanogaster* Schneider 2 (S2) cell line (American Type Culture Collection (ATCC) No. CRL-1963), *D. melanogaster* Kcl cells, gypsy moth cell line, IPLB-LdElta (Ld), *S. frugiperda* cell lines, IPLB-SF21AE (Sf21) and Sf9 (ATCC No. CRL-1711), and *Trichloplusia ni* cell lines Tn368 and BT1-TN5b1-4 (High Five), all of which are known in the art. Yeast cells can be used for vaccine or pharmaceutical product expression. Production and purification of the gene product may be achieved and enhanced using known techniques. Combining various nucleic acid sequences in a cloning vector can produce mosaic peptides.

Examples of appropriate cloning and sequencing techniques, and instructions sufficient to direct persons of skill through many cloning exercises are found in Berger and Kimmel, *Guide to Molecular Cloning Techniques*, Methods in Enzymology volume 152 Academic Press, Inc., San Diego, Calif.; Sambrook et al. (1989) *Molecular Cloning—A Laboratory Manual* (2nd ed.) Vol. 1-3, Cold Spring Harbor Laboratory Press, Cold Spring Harbor, N.Y.; and *Current Protocols in Molecular Biology*, F. M. Ausubel et al., eds., Current Protocols, a joint venture between Greene Publishing Associates, Inc. and John Wiley & Sons, Inc., (1994 Supplement). Product information from manufacturers of biological reagents and experimental equipment also provide information useful in known biological methods.

Provided with the T24 peptide sequences described herein, one of skill will recognize a variety of equivalent nucleic acid molecules that encode the peptides. This is because the genetic code requires that each amino acid residue in a peptide is specified by at least one triplet of nucleotides in a nucleic acid which encodes the peptide. Due to the degeneracy of the genetic code, many amino acids are equivalently coded by more than one triplet of nucleotides. For instance, the triplets CGU, CGC, CGA, CGG, AGA, and AGG all encode the amino acid arginine. Thus, at every position where an arginine is to be encoded by a nucleic acid triplet, the nucleic acid can have any of the triplets that encode arginine. One of skill is thoroughly familiar with the genetic code and its use (for example see chapter 15 of Watson, et al., *Molecular Biology of the Gene* ($4^{th}$ Ed., The Benjamin/Cummings Company, Inc., Menlo Park, Calif., 1987), and references cited therein).

Although any nucleic acid triplet or codon that encodes an amino acid can be used to specify the position of the amino acid in a peptide, certain codons are preferred by certain organisms. In some examples, it is desirable to select codons for elevated expression of an encoded peptide, for example, when the peptide is purified for use as an immunogenic reagent. Codons can be selected by reference to species codon bias tables, which show which codons that are most typically used by the organism (such as an insect) in which the peptide is to be expressed. The codons used frequently by an organism are translated by the more abundant t-RNAs in the cells of the organism. Because the t-RNAs are abundant, translation of the nucleic acid into a peptide by the cellular translation machinery is facilitated.

Conservative variations of a T24 nucleic acid molecule can yield a functionally identical construct. For example, due to the degeneracy of the genetic code, silent substitutions (substitutions of a nucleic acid sequence that do not result in an alteration in an encoded peptide) are an implied feature of every nucleic acid sequence which encodes an amino acid. In addition, one of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (such as in conjunction with ligation or cloning to generate large nucleic acids) and other well-known techniques. See, Giliman and Smith, *Gene* 8:81-97, 1979; Roberts et al., *Nature* 328:731-4, 1987; and Sambrook, Ausbel, Berger and Kimmel, all supra.

Modifications to nucleic acids are evaluated by routine screening techniques in suitable assays for the desired characteristic. For instance, changes in the immunological character of encoded peptides can be detected by an appropriate immunological assay. Modifications of other properties such as nucleic acid hybridization to a complementary nucleic acid, redox or thermal stability of encoded proteins, hydrophobicity, susceptibility to proteolysis, or the tendency to aggregate are all assayed according to standard techniques.

Making and Identifying T24 Antigenic Fragments

To identify T24 antigenic fragments, synthetic or recombinant T24 peptides are generated. In one example, such peptides are about 200 amino acids, about 150 amino acids, about 100 amino acids, about 92 amino acids, about 90 amino acids, about 50 amino acids, about 25 amino acids, about 15 amino acids, or about 10 amino acids. The peptides can be absorbed to a plastic microwell, nitrocellulose, other membranes, or any other appropriate support. A peptide can be cross-linked to itself using a cross-linking agent, such as glutaraldehyde or cross-linked to a carrier protein, such as albumin, keyhole-limpet hemocyanin prior to absorption to the support. Antibodies present in body fluids from patients with cysticercosis or monoclonal antibodies specific for *T. solium* antigens bind the antigenic peptides or polypeptides and are detected using any immunoassay described below. Reactivity with the antibodies identifies an antigenic fragment.

Smaller T24 peptides can be linked together to form polypeptides ranging in size from 40-200 amino acids using chemical ligation.

*T. solium* T24 Nucleic Acid Molecules

Nucleic acid molecules encoding a *T. solium* T24 peptide, and probes or primers that hybridize to nucleic acid molecules encoding a T24 peptide, are provided. These nucleotides include DNA, cDNA and RNA sequences that encode for a T24 peptide.

It is understood that all nucleotides encoding a T24 peptide are also included herein, as long as they encode a polypeptide with the recognized activity, such as the ability to elicit or stimulate an immune response, react with a T24 antibody (such as those found in subjects having a *T. solium* infection), or combinations thereof T24 nucleotides include sequences that are degenerate as a result of the genetic code, as long as the T24 amino acid sequence encoded by the nucleotide sequence is not substantially functionally changed. Nucleotide sequences encoding a T24 peptide also includes conservative variations thereof.

The disclosure provides isolated T24 nucleic acid sequences that contain a variation of a T24 sequence, such as a variant T24 nucleic acid sequence. Variants can contain a single insertion, a single deletion, a single substitution, multiple insertions, multiple deletions, multiple substitutions, or any combination thereof (such as a single deletion together with multiple insertions) as long as the peptide encoded thereby retains T24 activity. It will be understood by those ordinarily skilled in the art that the *T. solium* T24 polypeptides described herein are also encoded by sequences substantially similar to the nucleic acid sequences provided herein.

In a particular example, a T24 nucleic acid includes SEQ ID NO: 1, nucleotides 33-707 of SEQ ID NO: 1, or nucleotides 342-617 of SEQ ID NO: 1, or sequences including at least 85%, at least 90%, at least 95%, or at least 98% sequence identity to SEQ ID NO: 1, nucleotides 33-707 of SEQ ID NO: 1, or nucleotides 342-617 of SEQ ID NO: 1. For example, the following variations can be made to a T24 nucleic acid sequence shown in SEQ ID NO: 1, the "t" at position 53 can be substituted with a "a," "g," or "c"; the "c" at position 101 can be substituted with an "a" or "t"; the "c" at position 293 and 341 can be substituted with a "g" "t" or "a;" and the "a" at position 533; can be substituted with a "g."

In another example, a T24 nucleic acid molecule includes at least 23 contiguous nucleotides of SEQ ID NO: 1, for example at least 25, at least 50, at least 100, at least 200, at least 275, at least 500, at least 700, or even at least 800 contiguous nucleotides of SEQ ID NO: 1. In some examples, such fragments can selectively hybridize under physiological conditions to a nucleic acid sequence that encodes a T24 peptide, such as a polynucleotide that encodes SEQ ID NO: 2. The term "selectively hybridize" refers to hybridization under moderately or highly stringent conditions which excludes non-related nucleotide sequences.

T24 nucleic acid molecules are useful for producing T24 recombinant polypeptides. Because recombinant polypeptide production can produce large quantities of polypeptide that require less purification, recombinant polypeptides are often less expensively produced than polypeptides produced using traditional isolation or purification techniques. A nucleic acid sequence encoding for a *T. solium* T24 peptide can be inserted into a vector, into an autonomously replicating plasmid or a virus, into the genomic DNA of a prokaryote or eukaryote, or which exists as a separate molecule (such as a cDNA) independent of other sequences such as a plasmid, and recombinantly expressed in a host cell. The term host cell also includes any progeny of the subject host cell. It is understood that all progeny may not be identical to the parental cell since there may be mutations that occur during replication. Methods of expressing DNA sequences in host cells are well known in the art.

T24 polynucleotide sequences can be inserted into an expression vector including, but not limited to a plasmid, virus or other vehicle that has been manipulated by insertion or incorporation of a T24 nucleic acid sequence. Polynucleotide sequences that encode for T24 can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon in front of a protein-encoding gene, splicing signal for introns, maintenance of the correct reading frame of that gene to permit proper translation of mRNA, and stop codons. The term "control sequences" includes, at a minimum, components whose presence can influence expression, and can also include additional components whose presence is advantageous, for example, leader sequences and fusion partner sequences. Expression control sequences can include a promoter.

Exemplary promoters include a minimal sequence sufficient to direct transcription. Also included are promoter elements which are sufficient to render promoter-dependent gene expression controllable for cell-type specific, tissue-specific, or inducible by external signals or agents; such elements may be located in the 5' or 3' regions of the gene.

Constitutive and inducible promoters can be used (Bitter et al., *Meth. Enzymol.* 153:516-44, 1987). For example, when cloning in bacterial systems, inducible promoters such as pL of bacteriophage γ, plac, ptrp, ptac (ptrp-lac hybrid promoter) and the like can be used. When cloning in mammalian cell systems, promoters derived from the genome of mammalian cells (such as a metallothionein promoter) or from mammalian viruses (such as the retrovirus long terminal repeat; the adenovirus late promoter; the vaccinia virus 7.5K promoter) can be used. When cloning in insect cell systems, promoters derived from the genome of insect cells (such as OpIE2 for constitutive expression or the metallothionein promoter for inducible expression) can be used. Promoters produced by recombinant DNA or synthetic techniques can also be used to provide for transcription of the nucleic acid sequences of the disclosure.

The polynucleotide encoding a T24 peptide can be inserted into an expression vector which contains a promoter sequence which facilitates the efficient transcription of the inserted genetic sequence of the host. The expression vector typically contains an origin of replication, a promoter, as well as specific genes which allow phenotypic selection of the transformed cells. Vectors suitable for use include, but are not limited to the T7-based expression vector for expression in bacteria (Rosenberg et al., 1987, *Gene* 56:125), the pMSXND expression vector for expression in mammalian cells (Lee and Nathans, *J. Biol. Chem.* 263:3521, 1988), pIZ/V5-His (Invitrogen) and pMIB/V5-His A (Invitrogen) for expression in insect cells, and baculovirus-derived vectors for expression in insect cells.

Transformation of a host cell with recombinant DNA can be performed using conventional techniques well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, for example an insect cell, methods of transfection of nucleic acid molecules include calcium phosphate co-precipitates, conventional mechanical procedures such as microinjection, electroporation, insertion of a plasmid encased in liposomes, or use of a viral vectors. Eukaryotic cells can also be cotransformed with DNA sequences encoding a T24 peptide, and a second exogenous DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (*Eukaryotic Viral Vectors*, Cold Spring Harbor Laboratory, Gluzman ed., 1982).

The resulting recombinantly expressed T24 peptide can be isolated and purified using conventional methods, for example preparative chromatography and immunological separations involving monoclonal or polyclonal antibodies.

T24 nucleic acid molecules (and fragments or variants thereof) are also useful as nucleic acid probes or primers for the detection of *T. solium* infection in a biological sample, with high sensitivity or specificity. The probes or primers can be used to amplify or detect *T. solium* larvae nucleic acid molecules in the sample, quantify the amount of *T. solium* in the sample, diagnose infection or determine contamination with *T. solium*, or monitor the progress of therapies used to treat the infection. T24 nucleic acid molecules are also useful to study the *T. solium* organism and diseases associated with this organism (such as cystercercosis and neurocystercercosis) and to develop therapies and treatments for such diseases. In some examples, T24 nucleic acid molecules are labeled with a detectable label.

Also provided herein are sequences, probes and primers that selectively hybridize to the encoding nucleic acid or the complementary, or opposite (or antisense), strand of nucleic acid as those specifically provided herein. Specific hybridization with a nucleic acid can occur with minor modifications or substitutions in the nucleic acid, so long as functional, species-specific hybridization capability is maintained.

Hybridization can be achieved under various temperatures and conditions, according to the temperature of dissociation ($T_d$) of the molecules being hybridized and the stringency required for specific binding. The molecules can be hybridized to one another in any order or at the same or essentially the same time. Reaction conditions for hybridization of an oligonucleotide, or polynucleotide, to a nucleic acid sequence vary from oligonucleotide to oligonucleotide, depending on factors such as oligonucleotide length, the number of G and C nucleotides, and the composition of the buffer utilized in the hybridization reaction.

Moderately stringent hybridization conditions are when the hybridization is performed at about 42° C. in a hybridization solution containing 25 mM $KPO_4$ (pH 7.4), 5×SSC, 5× Denhart's solution, 50 μg/mL denatured, sonicated salmon sperm DNA, 50% formamide, 10% dextran sulfate, and 1-15 ng/mL probe (such as about $5×10^7$ cpm/μg), while the washes are performed at about 50° C. with a wash solution containing 2×SSC and 0.1% sodium dodecyl sulfate (SDS).

Highly stringent hybridization conditions are when the hybridization is performed at about 42° C. in a hybridization solution containing 25 mM $KPO_4$ (pH 7.4), 5×SSC, 5×Denhart's solution, 50 μg/mL denatured, sonicated salmon sperm DNA, 50% formamide, 10% dextran sulfate, and 1-15 ng/mL probe (such as about $5×10^7$ cpm μg), while the washes are performed at about 65° C. with a wash solution containing 0.2×SSC and 0.1% SDS.

If used as primers, T24 nucleic acid molecule compositions can include at least two nucleic acid molecules that hybridize to different regions of the T24 target molecule so as to amplify a desired region of T24. Depending on the length of the probe or primer, the target region can range between 85% complementary bases and full complementarity and still hybridize under stringent conditions. In specific examples, the hybridizing nucleic acid probes or primers described herein have at least 85%, at least 90%, at least 95%, at least 97%, at least 98%, or at least 99% complementarity with the segment of the sequence to which they hybridize, for instance 85% or more. For the purpose of determining the presence of *T. solium*, the degree of complementarity between the hybridizing nucleic acid (probe or primer) and the sequence to which it hybridizes is at least enough to distinguish hybridization with a nucleic acid from other organisms. In particular examples, a probe or primer is a DNA molecule having a length of 20 to 40 nucleotides, such as 25 to 35 nucleotides.

Amplification of synthesized T24 DNA can be detected by any method used in the art. Exemplary detection methods include Southern blot hybridization, visualization of DNA amplification products of specific molecular weight on ethidium bromide stained agarose gels, measurement of the incorporation of radiolabeled nucleotides into the synthesized DNA strand by autoradiography or scintillation measurement, and ELISA modified for the capture of a detectable moiety bound to the amplified DNA. One particular detection method is hybridization of the amplified DNA to an internal specific oligo-probe using ELISA, Southern blot hybridization or similar methods.

Labeled T24 *T. solium* Polypeptides

When labeled with a detectable biomolecule or chemical, a *T. solium* T24 peptide, including antigenic fragments thereof, are useful for diagnostic methods and assays described below. Various types of labels and methods of conjugating the labels to the polypeptides are well known. Several exemplary labels are set forth below.

For example, a T24 peptide can be conjugated to a radiolabel such as, but not limited to, $^{32}P$, $^{3}H$, $^{14}C$, $^{35}S$, $^{125}I$, or $^{131}I$. Detection of a label can be by methods such as scintillation counting, gamma ray spectrometry or autoradiography.

Bioluminescent labels, such as derivatives of firefly luciferin, can also be used. The bioluminescent substance is covalently bound to the polypeptide by conventional methods, and the labeled polypeptide is detected when an enzyme, such as luciferase, catalyzes a reaction with ATP causing the bioluminescent molecule to emit photons of light.

Fluorophores can also be used as labels. Examples of fluorophores include fluorescein and derivatives, phycoerythrin, allo-phycocyanin, phycocyanin, rhodamine, and Texas Red. Fluorophores can be excited using an appropriate laser or filter and detected using a fluorescence detector.

The T24 polypeptides can also be labeled with a chromogen to provide an enzyme or affinity label. For example, the polypeptide can be biotinylated so that it can be utilized in a biotin-avidin reaction, which can also be coupled to a label such as an enzyme or fluorogen. Alternatively, the polypeptide can be labeled with peroxidase, alkaline phosphatase or other enzymes giving a chromogenic or fluorogenic reaction upon addition of substrate. Additives such as 5-amino-2,3-dihydro-1,4-phthalazinedione (also known as Luminol™) (Sigma, St. Louis, Mo.) and rate enhancers such as p-hydroxybiphenyl (also known as p-phenylphenol) (Sigma) can be used to amplify enzymes such as horseradish peroxidase through a luminescent reaction; and luminogenic or fluorogenic dioxetane derivatives of enzyme substrates can also be used. Such labels can be detected using enzyme-linked immunoassays (ELISA) or by detecting a color change with the aid of a spectrophotometer. In addition, peptides can be labeled with colloidal gold for use in immunoelectron microscopy in accordance with methods well known to those skilled in the art.

The diagnosis of an infection by *T. solium* larvae can be determined by labeling a T24 peptide as described above, incubating the labeled peptide with a sample, and detecting the label. The presence of detectable label indicates that the sample contains (or has been exposed to) *T. solium* larvae, while the absence of detectable label indicates that the sample does not contain (or has not been exposed to) *T. solium* larvae.

Detection of T24 *T. solium* Antibodies

Many methods are known for detecting and quantifying a component, such as an antibody in a mixture, or for measuring its amount. Immunoassays, which employ peptides that bind specifically to antibodies of interest, can be used. These methods permit detection (or quantification) of *T. solium* antibodies present in a subject to indicate the presence or level of *T. solium* infection, and in some examples the diagnosis of a disease or condition associated with such infection, for example cysticercosis. Exemplary methods involve contacting a biological sample containing the antibody with a known excess amount of peptide specific for the antibody, such as a disclosed T24 peptide, separating bound from free antibody, and determining the amount of one or the other, for example by detecting a label on the T24 peptide or by incubating with a secondary antibody. The second antibody can be labeled to aid in the determination of the amount of bound analyte as described above.

In one example, the diagnostic method uses a rapid immunochromatographic diagnostic test (card test) assay. In a further example, the diagnostic method is a rapid card test assay including one or more larval *T. solium* protein antigens, such as T24, or an antigenic fragment thereof.

The assay methods can include the use of synthetic or recombinant T24 *T. solium* peptides as described above, as well as fusions, fragments or variants of the *T. solium* T24 peptide described herein as long as the fusions, fragments or variants retain immunogenic activity, the ability to immunoreact with a T24 antibody, or combinations thereof. These fusions, fragments or variants include T24 peptides with antigenic activity that have amino acid substitutions or have other molecules attached to amino acid functional groups as described above. In some examples, the assay methods include the use of one or more other synthetic or recombinant *T. solium* larval peptides, or fusions, fragments or variants thereof. These other polypeptides include, but are not limited to, gp50, gp39-42, gp21, gp18, gp14 and gp13 (see U.S. Pat. No. 5,354,660, herein incorporated by reference).

An immunoassay for the detection of *T. solium* in a sample can be performed as follows. To detect *T. solium* antibodies in a sample, such as T24 antibodies, the sample is incubated with one or more *T. solium* recombinant or synthetic peptides, such as the T24 peptides disclosed herein. The peptide can be labeled or conjugated to a solid phase bead or particle as described herein. The labeled peptide is detected using well known techniques for detection of biologic molecules, such as immunochemical or histological methods. For example, immunological techniques employing monoclonal or polyclonal antibodies to the polypeptide, such as enzyme linked immunosorbant assays, radioimmunoassay, chemiluminescent assays, or other types of assays involving antibodies can be used.

The sample potentially containing the *T. solium* antibodies to be detected can be collected or obtained from a subject using methods well known to those skilled in the art. The sample can be obtained from any biological source, such as blood serum, blood plasma, urine, spinal fluid, saliva, fermentation fluid, lymph fluid, tissue culture fluid and ascites fluid. In addition, the sample can be diluted, purified, concentrated, filtered, dissolved, suspended, or otherwise manipulated prior to immunoassay.

In general, binding assays rely on the binding of analyte by analyte receptors to determine the concentrations of analyte in a sample. These immunoassays can be described as either competitive or non-competitive. Non-competitive assays generally utilize analyte receptors in substantial excess over the concentration of analyte to be determined in the assay. Sandwich assays are examples of non-competitive assays, which include one analyte receptor frequently bound to a solid phase and a second analyte receptor labeled to permit detection. The analyte first binds to the analyte receptor bound to a solid phase and the second labeled analyte receptor is then added to facilitate quantitation of the analyte. Bound analyte can easily be separated from unbound reagents, such as unbound labeled first analyte receptors, due to the use of an analyte receptor bound to a solid phase.

Competitive assays generally involve a sample suspected of containing analyte, an analyte-analogue conjugate, and the competition of these species for a limited number of binding sites provided by the analyte receptor. Competitive assays can be homogeneous or heterogeneous. In homogeneous assays all reactants participating in the competition are mixed together and the quantity of analyte is determined by its effect on the extent of binding between analyte receptor and analyte-conjugate or analyte analogue-conjugate. The signal observed is modulated by the extent of this binding and can be related to the amount of analyte in the sample.

Methods are also disclosed for the diagnosis or prognosis of cysticercosis. A determination of the presence of larval *T. solium* antibodies, such as a T24 antibody, can be made using the recombinant or synthetic T24 polypeptides or antigenic fragments thereof described herein as reagents in assays using assay techniques that are well known to those skilled in the art and include methods such as rapid immunochromatographic diagnostic tests, Western blot analysis, radioimmunoassay and ELISA assays. For example, a sample can be incubated with a *T. solium* protein, such as a T24 protein, for a time sufficient to allow the protein and antibodies in the sample to bind, and detecting binding of the protein with the antibodies. The protein can be labeled to permit detection of protein:antibody complexes. Alternatively, protein:antibody complexes can be detected by using a labeled secondary antibody. The presence of detectable protein:antibody complexes indicates that the subject has cysticercosis, while the absence of detectable protein:antibody complexes indicates that the subject does not have cysticercosis. A decrease in detectable protein: antibody complexes can indicate that the subject is recovering from cysticercosis. Samples can be obtained, for instance, from the blood, cerebrospinal fluid, urine, saliva, or tissues of a mammal, such as a human or pig.

Detection of T24 *T. solium* Proteins and Nucleic Acid Molecules

The disclosure herein of T24 protein and nucleic acid sequences permits one to detect such sequences in a sample. These methods permit detection (or quantification) of *T. solium* protein and nucleic acid sequences present in a subject to indicate the presence or level of *T. solium* infection, and in some examples the diagnosis of a disease or condition associated with such infection, for example cysticercosis.

Exemplary methods include contacting a biological sample containing T24 nucleic acid sequences with a probe or primer that can recognize the T24 nucleic acid sequence. In some examples, nucleic acid molecules present in the sample are first isolated prior to contacting with the probe or primer. For example, nucleic acid molecules can be isolated and transferred to a membrane (such as nitrocellulose), which is incubated with a probe that recognizes T24 sequences. In one example, a probe containing a detectable label is incubated with the sample for a period time to allow hybridization between the probe and T24 nucleic acid molecules. The presence of probe:T24 nucleic acid molecule complexes is then determined by detecting the label on the probe (wherein the presence of such complexes indicates that the subject has a *T. solium* infection, cysticercosis, neurocysticercosis, or combinations thereof). In a particular example, primers are used to amplify a T24 nucleic acid sequence from a sample. For example, PCR or RT-PCR can be used, and the presence of resulting amplicons determined. The presence of amplicons indicates that the subject has a *T. solium* infection, cysticercosis, neurocysticercosis, or combinations thereof.

Other methods involve contacting a biological sample containing T24 protein sequences with an antibody that can recognize the T24 protein. For example, the sample can be incubated with an antibody that recognizes a T24 protein, and the presence of antibody:protein complexes determined, for example by using microscopy, a spectrophotometer or flow cytometry. The presence of antibody:protein complexes indicates that the subject has a *T. solium* infection, cysticercosis, neurocysticercosis, or combinations thereof. In some examples, the antibody includes a label that permits detection of the complexes. In other examples, a labeled secondary antibody is used to detect the complexes.

In some examples, proteins present in the sample are first purified prior to contacting with an antibody. For example, the sample can be subjected to SDS-PAGE, and the proteins transferred to a membrane, such as nitrocellulose. The membrane is then incubated with the antibody, and the presence of antibody:protein complexes determined. The presence of antibody:protein complexes indicates that the subject has a *T. solium* infection, cysticercosis, neurocysticercosis, or combinations thereof. In some examples, the antibody includes a label that permits detection of the complexes. In other examples, a labeled secondary antibody is used to detect the complexes.

Control samples can include positive controls, for example sera known to be infected with *T. solium*, or a sample containing known T24 nucleic acid molecules or proteins. Control samples can include negative controls, for example sera known to be free of *T. solium*, a sample infected with another pathogen, or a sample that does not contain nucleic acid molecules or proteins.

Kits for Detecting *T. solium* or for Diagnosing a *T. solium*-Associated Condition Kits for detecting the presence or quantity of *T. solium* in a sample, or for diagnosis a *T. solium*-associated disease or condition, are also provided. The kits can be in any configuration useful for performing one or more of the assays described herein for the detection of *T. solium* in biological samples or for the detection or monitoring of *T. solium* infection in a patient or carrier. The kits are convenient in that they supply many, if not all, of the essential reagents for conducting an assay for the detection of *T. solium* in a biological sample. The reagents can be pre-measured and contained in a stable form in vessels or on a solid phase in or on which the assay can be performed, thereby minimizing the number of manipulations carried out by the individual conducting the assay. In addition, the assay can be performed simultaneously with a standard included with the kit, such as a predetermined amount of larval *T. solium* antigen or antibody, so that the results of the test can be validated or measured.

In certain examples, the kits contain recombinant or synthetic T24 *T. solium* peptides for the detection of T24 *T. solium* antibodies, or include T24 nucleic acid molecules to detect or amplify *T. solium* nucleic acid molecules present in a sample. The kit can further include one or more additional recombinant or synthetic *T. solium* larval polypeptides or nucleic acid molecules described herein. The kits can additionally contain the appropriate reagents for binding the polypeptides to the antibodies or hybridizing the nucleic acid molecules to their respective *T. solium* complementary nucleic acid molecules in the sample as described herein and reagents that aid in detecting the antibody-polypeptide or nucleic acid molecule complexes. The kits can contain equipment for safely obtaining the sample, a vessel for containing the reagents, a timing means, a buffer for diluting the sample, and a colorimeter, reflectometer, or standard against which a color change may be measured.

In specific examples, the reagents, including the T24 peptides, are lyophilized, for instance in a single vessel. Addition of aqueous sample to the vessel results in solubilization of the lyophilized reagents, causing them to react. In certain specific examples, the reagents are sequentially lyophilized in a single container, in accordance with methods that minimize reaction by the reagents prior to addition of the sample. Such methods are well known to those of ordinary skill in the art.

In some examples, the T24 peptides are present on a solid substrate, such as a membrane (for example nitrocellulose) or polystyrene. Such substrates can be incubated with a sample (such as a sample suspected of containing T24 antibodies), and the presence of a peptide:antibody complex determined.

Specific examples of assay kits include, but are not limited to, reagents to be employed in one or more of the following methods: competitive and non-competitive assays, radioimmunoassay, bioluminescence and chemiluminescence assays, fluorometric assays, sandwich assays, immunoradiometric assays, dot blots, enzyme linked assays including immunoblots and ELISAs, and immunocytochemistry. Materials used in conjunction with these techniques include, but are not limited to, microtiter plates, antibody (or T24 protein) coated strips or dipsticks for rapid monitoring of urine or blood. For each kit, the range, sensitivity, precision, reliability, specificity, and reproducibility of the assay are established.

In another example, the assay kit uses immunoblot techniques and provides instructions and one or more synthetic or recombinant larval *T. solium* polypeptides, such as T24, conjugated to a detectable molecule. The kit can be used to detect and measure *T. solium* in biological fluids and tissue extracts of animals and humans to diagnose or monitor cysticercosis or neurocysticercosis.

T24 Sequences as Immunogenic Compositions

Methods are provided for treating a subject having cysticercosis or neurocysticercosis, or preventing the development of cysticercosis or neurocysticercosis following *T. solium* infection. The method includes administering to the subject a therapeutically effective amount of one or more T24 epitopes (or nucleic acid encoding such an epitope), thereby treating cysticercosis or neurocysticercosis, for example by decreasing one or more symptoms associated with cysticercosis or neurocysticercosis. The T24 eptiope(s) can be administered in the presence of pharmaceutically acceptable carrier, alone or in the presence of an agent that aids in stimulation of the immune response, such as an adjuvant. In one example, the susceptibility of the subject to *T. solium* infection, such as a human or pig, is determined prior to administering a therapeutically effective amount of a T24 epitope.

Also disclosed are methods for eliciting an immune response in a subject. The method includes administering to the subject a therapeutically effective amount of one or more T24 epitopes (or nucleic acid encoding such an epitope), thereby eliciting an immune response in a subject. Specific, non-limiting examples of an immune response are a B cell or a T cell response. Methods of generating antibodies specific for a T24 antigen, are disclosed. The method includes administering to a subject one or more T24 antigens, such as SEQ ID NO: 2 or amino acids 104-195 of SEQ ID NO: 2. In one example, the subject is an experimental animal, such as a mouse or rabbit. In another example, the subject is a mammal, such as a pig or human.

In forming a pharmaceutical composition for eliciting an immune response in a subject, or for treating cysticercosis or neurocysticercosis, one or more T24 epitopes (at a therapeutically effective amount), alone or in combination with other agents, is utilized. T24 epitope variants, fragments, and fusions can be employed in the pharmaceutical compositions, and can include one or more amino acid additions, amino acid deletions, amino acid replacements, or by isostereomer (a modified amino acid that bears close structural and spatial similarity to the original amino acid) substitutions, and isostereomer additions, so long as the sequences are recognized by, or can generate, and immune cell. For example, a variant of SEQ ID NO: 2, such as amino acids 104-195 of SEQ ID NO: 2, will be recognized by an immune cell that recognizes SEQ ID NO: 2. In a particular example, such variants, fragments, and fusions, provide an advantage, such as increasing the solubility or immungenicity of the eptitope, or easing linking or coupling of the epitope. In one example, the peptides included in the pharmaceutical composition can form neutralizing antibodies to a T24 epitope.

The disclosed T24 peptides can be engineered to include other amino acids (to generate a fusion protein), such as residues of various moieties, such as additional amino acid segments or polysaccharides. Examples include, but are not limited to, moieties which augment or induce antigen processing, epitope stability or manufacture, or delivery within the body to sites appropriate for immunization or recognition by immune cells. In addition, an amino acid chain corresponding to an additional antigen or immunogen can be included. Thus, an immune response to more than one antigen can be induced by immunization. Specific non-limiting examples of antigens or immunogens include, but are not limited to, other *T. solium* larval proteins that increase or provoke $CD4^+$ T-cell (helper T-cell) responses supportive of a T24 immune response. These additional amino acid sequences can be of varying length.

In some examples, it is desirable to combine two or more T24 epitopes that contribute to stimulating specific immune responses in one or more subjects or histocompatibility types. The epitopes in the composition can be identical or different, and together they may provide equivalent or greater biological activity than the parent epitopes(s). For example, multiple epitopic peptides can be combined in a "cocktail" to provide enhanced immunogenicity, and peptides can be combined with peptides having different MHC specificities. Such compositions can be used to effectively broaden the immunological coverage provided by therapeutic, immune stimulatory composition or diagnostic methods and compositions.

In some examples, epitopic peptides are linked with or without a spacer molecule to form polymers (multimers), or can be formulated in a composition without linkage, as an admixture. Where the same peptide is linked to itself, thereby forming a homopolymer, a plurality of repeating epitopic units are presented. When the peptides differ, heteropolymers with repeating units are provided.

Linkages for homo- or hetero-polymers or for coupling to carriers and adjuvants can be provided in a variety of ways, such as through covalent linkages between epitopic peptides or noncovalent linkages capable of forming intermolecular and intrastructural bonds. When present, the spacer can include relatively small, neutral molecules, such as amino acids or amino acid mimetics, which are substantially uncharged under physiological conditions and may have linear or branched side chains. Particular examples of spacers include on or more alanine or glycine residues, or other nonpolar amino acids or neutral polar amino acids. Spacers can be either homo- or hetero-oligomers and can include one or two residues, more typically three to six residues. Spacers can be attached to epitopic peptides at the C-terminus, N-terminus or a side chain of one or more of the amino acids.

Examples of crosslinking agents which can be used to interconnect a plurality of epitopes include crosslinking agents which have as their functional group an aldehyde (such as glutaraldehyde), carboxyl, amine, amido, imido or azidophenyl group. In particular, butyraldehyde can be used as a crosslinking agent, a divalent imido ester or a carbodiimide.

In another example, cysteine residues can be added at the amino- and carboxy-termini to permit formation of bonds between peptides via controlled oxidation of the cysteine residues. Heterobifunctional agents, which generate a disulfide link at one functional group end and a peptide link at the other, including N-succidimidyl-3-(2-pyridyldithio) proprionate (SPDP) may also be employed. A variety of such disulfide/amide forming agents are known (For example, Immun. Rev. 62:185, 1982). Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, and 4-(N-maleimidomethyl) cyclohexane-1-carboxylic acid. In these reagents, the carboxyl groups can be activated by combining them with succinimide or 1-hydroxy-2-nitro-4-sulfonic acid, sodium salt. One coupling agent is succinimidyl 4-(N-maleimidomethyl)cyclohexane-1-carboxylate (SMCC). Ideally, the linkage does not substantially interfere with the immunogenicity of the linked epitopic peptides.

A particular example of a fusion protein, which includes one or more T24 epitopic peptide sequences, can be used to present the epitopic peptides to a subject. For example, a recombinant HBV surface antigen protein is prepared in which the HBenv amino acid sequence is altered so as to more effectively present epitopes of peptide regions described herein to stimulate an immune response. By this means a polypeptide may incorporate several epitopes. Coding sequences for peptides of the length contemplated herein can be synthesized by chemical techniques, for example, the phosphotriester method of Matteucci et al. (*J. Am. Chem. Soc.* 103:3185, 1981). The coding sequence can then be provided with appropriate linkers and ligated into expression vectors commonly available in the art, and the vectors used to transform suitable hosts to produce the desired fusion protein as disclosed herein and known in the art.

In one example, the disclosed T24 epitopes, such as SEQ ID NO: 2 or a fragment thereof, such as amino acids 104-195 of SEQ ID NO: 2, is obtained from natural sources, chemically synthesized, or produced recombinantly. The T24 protein is subjected to selective proteolysis, for example by splitting the protein with chemical reagents or enzymes. The length of the amino acid sequence produced can depend on the method of producing the sequence. If the sequence is made by assembling amino acids by chemical means, the sequence ideally does not exceed, for example, about 50, about 40, or about 30 amino acids. If the synthetic peptide is made by translating a nucleic acid, the peptide can be any length, including, for example, about 100 amino acids or more. However, the peptide can also be shorter, for example, no more than 50, no more than 40, no more than 20, no more than 10, no more than 9, or no more than 8 amino acids, for example about 8-50 amino acids.

This disclosure is further illustrated by the following Examples, which are not to be construed in any way as imposing limitations upon the scope of the disclosure. It is understood that resort may be had to various other embodiments, modifications, and equivalents thereof that, after reading the description herein, may suggest themselves to those of ordinary skill in the art, without departing from the spirit of the present disclosure or the scope of the appended claims.

EXAMPLE 1

Cloning and Analysis of T24 kDa from *T. solium*

This example describes the methods used to purify and clone T24 (LLGP24) from Triton X-114 extracted *T. solium* cysticerci or from lentil lectin purified glycoprotein (LLGP). Although the molecular weight of several *T. solium* larval proteins was previously known, the sequence of T24 had not been identified. Purification and cloning of T24 proved difficult, because several proteins (about nine) co-migrated at the same position on SDS-PAG. Therefore, the T24 protein was not previously substantially purified, even though its molecular weight on an SDS-PAG was known. It is likely that previous preparations of T24, even on SDS-PAG, were only about 30% pure by weight, due to the contaminating proteins that co-migrate in this region. Determining the sequence of T24 is important to permit recombinant expression of T24 to allow for the development of a less-expensive diagnostic assay for *T. solium* infection.

Purification and Cloning from Triton X-114 Extracted *T. solium* Cysticerci

Approximately 200 mg of *T. solium* cysts were homogenized, extracted with the detergent Triton X-114, and the proteins were separated by phase partitioning into an aqueous phase and a detergent phase. Proteins in the detergent phase are membrane proteins. The proteins in each phase were analyzed by silver staining and western blotting (FIGS. 1 and 2A). Proteins immunoreactive with TSC-1 (pool sera from three parasitologically confirmed cysticercosis patients) were observed in the detergent phase at 24-, 42-, and 50-kDa. Their size, immunoreactivity with TSC-1 and a panel of cysticercosis positive sera, and susceptibility to DTT reduction were confirmed by silver staining and western blotting.

Approximately 200 μg of the fraction containing T24 and T42 were acetone precipitated, resolved by SDS-PAGE, blotted onto PVDF membrane, and the bands at 24- and 42-kDa excised using a corresponding western blot as the guide. Approximately 390 μg of the same fraction was acetone precipitated, resolved by SDS-PAGE, stained with Colloidal Coomassie Stain, and the bands at 24- and 42-kDa excised and sequenced.

The N-terminus of the proteins on PVDF was sequenced by Edman degradation. The N-terminus sequences of both proteins were identical. The proteins in the gel slice were digested with trypsin and the tryptic peptides were analyzed by MS/MS spectra using the Sequest algorithm. However, the MS/MS data were not informative. The four tryptic peptides of T24 from the gel slice were subsequently sequenced using Edman degradation. Five internal peptide sequences were obtained by denovo MS/MS sequencing of the T42 sample. All five of the T42 peptide sequences are within the coding sequence of T24.

A search of the BLAST nr and est databases with the N-terminal sequence and with one of the internal sequences from T24 identified several *Echinococcus granulosus* EST sequences (Genbank Accession Nos: B1244014, BF643023, BQ173431, BQ173376, BG173191, and BQ173064). The sequences shown in Genbank Accession Nos: BI244014 and BF643023 appear to overlap and form an ORF beginning with the initiating methionine. All of the peptide sequences share homology to the *E. granulosus* EST sequences.

Purification and Cloning from LLGP

T24/T42 (LLGP24/LLGP42) was purified from LLGP as follows. Approximately 2.5 mg of LLGP, lot Ts10322, were subjected to preparative SDS-PAGE using a Model 491 Prep Cell (BioRad). One hundred fifty fractions were collected and analyzed by silver staining and western blotting. Based on size, fractions 40-48 were pooled to form the LLGP24 pool and fractions 78-90 were pooled to form the LLGP42 pool. Proteins were concentrated by acetone precipitation. Their size, immunoreactivity with a pool of cysticercosis infection sera (TSC-1), and susceptibility to DTT reduction were confirmed by silver staining and western blotting.

Approximately half of each pool was resolved by SDS-PAGE, blotted onto PVDF membrane, and the bands at 24- and 42-kDa were excised using a corresponding western blot as the guide. The other half of each pool was resolved by SDS-PAGE, stained with Colloidal Coomassie Stain (Invitrogen), and the bands at 24- and 42-kDa were excised. The N-terminus of the proteins on PVDF was sequenced by Edman degradation. The proteins in the gel slice were digested with trypsin and the tryptic peptides were analyzed by MS/MS spectra using the Sequest algorithm. This was followed by Edman degradation sequencing of four tryptic peptides for LLGP24 and one tryptic peptide for LLGP42.

Results

Sequences from several non-T24 proteins were identified from purification from LLGP, when N-terminal sequencing, Edman degradation, or MS/MS spectra were used. This made identification of T24 sequences difficult. The MS/MS spectra data provided several sequences, including: T24 and the 8-kDa family of proteins (Ts14, Ts18var1, Ts low molecular weight antigen 1, Ts low molecular weight antigen 2), but did not generate any new sequences. T24 would not have been identified in the sequences of the LLGP proteins at 24 kDa had it not already been cloned from the triton-extracted T24, because MS/MS spectra and the Sequest algorithm can only identify spectra from known sequences. Triton X-114 purified T24 and T42 were sequenced. Edman degradation sequencing of four tryptic peptide fragments from T24 and of the N-terminus was performed. De novo MS sequencing of T42 gave five sequences and all were within the cloned T24 cDNA. In the final cloned T24, nine of these 10 peptides sequences, five from T24 sequences and five from T42 sequencing, are within the predicted mature protein sequences. The tenth could not be identified.

The results for LLGP are summarized in Tables 1 and 2.

TABLE 1

Sequences identified from LLGP-24 band

| N-terminal sequencing | MS/MS spectra of Tryptic Peptides | Edman degradation of Tryptic Peptides |
|---|---|---|
| Ts14 (mature N terminus) AJ012670 (NC-9) (internal fragment) | T24, 16 spectra, 9.3e4 Ts14, 13 spectra, 3.3e4 Ts18var1, 7 spectra, 4.2e4 AB044080 (TsRS2 clade), 4 spectra, 1.2e4 AJ012670 (NC-9), 7 spectra, 4.7e4 AB044082 (TsRS1 clade), 5 spectra, 5.6e4 AJ012669 (NC-3), 5 spectra, 1.0e4 Echino P-29, 4 spectra, 4.8e3 AF523312 (oncosphere-specific antigen, related to 8-kDa proteins), 2 spectra, 2.7e3 | peptide 67 - 8-kDa protein (matches with Ts14 and TsRS2 sequences) peptide 71 - 8-kDa protein (matches with only Ts18 sequences) peptide 86 - AJ012670 (NC-9) and a secondary sequence with no hits peptide 94 - AJ012670 (NC-9), a secondary sequence that matches lectin, and a tertiary sequence with no hits |

TABLE 2

Sequences identified from LLGP-42 band

| N-terminal sequence* | MS/MS spectra of Tryptic Peptides | Edman degradation of Tryptic Peptides |
|---|---|---|
| Ts14 (mature N terminus) AJ012670 (NC-9) (internal fragment) | Ts18var1, 6 spectra, 1.1e4 Echino P-29, 5 spectra, 2.5e3 Ts14, 3 spectra, 8.7e2 T24, 1 spectra, 4.7e2 AJ012670 (NC-9), 1 spectra, 2.0e3 | AJ012670 (NC-9) |

Based on the N-terminal sequence and MS/MS spectra results, it appears that the 8-kDa proteins are components of LLGP-24 and LLGP-42. The predominant 8-kDa proteins were Ts14 and Ts18var1; however, Genbank Accession Nos: AB044082 (TsRS1 clade) and AB044080 (TsRS2 clade) were also observed. T24 was the predominant protein in the MS/MS spectra of LLGP-24, and was also observed in the MS/MS spectra of LLGP-42.

AJ012670 (NC-9) was a significant component present in LLGP-24 and LLGP-42. However, it is known that the sensitivity of a GST-NC-9 recombinant protein for detecting cysticercosis is only 33.3%. E. granulosus P-29 (Genbank Accession NO. AF078931) was to a lesser extent a significant component of LLGP-24 and LLGP-42. P-29, NC-9, and NC-3 were also observed in the MS/MS spectra of T24. P-29 was observed in the MS/MS spectra of T42.

These results also demonstrate that T24 is the impure component previously identified as LLGP-24. LLGP-24 is a well-characterized component of the LLGP diagnostic antigen used for more than ten years as the diagnostic gold-standard for the disease cysticercosis, caused by the larval stage of *T. solium*. LLGP is purified from urea-solubilized *T. solium* cysts (harvested from pig muscle). The urea-solubilized proteins are dialyzed into the appropriate buffer and run on a lentil lectin affinity column. The T24 diagnostic antigen is the bound fraction from this column. However, as described above, T24 can also be obtained from the detergent soluble fraction of a Triton X-114 extraction of cysts. In addition, the sequencing data indicates that T42 is a dimer of T24. LLGP-42 is a component of the diagnostic antigen band 39-42.

Based on the sequences obtained using these methods, T24 was cloned using the protein sequence data obtained from N-terminal and internal sequences of the Triton-extracted protein. Using a degenerate forward primer based on the N-terminal sequence and degenerate reverse primers based on the internal peptide sequence, a portion of the cDNA was amplified using a *T. solium* cDNA library prepared from cysts as the template. The full-length cDNA was obtained by random prime labeling of the partial sequence and probing the cDNA library. Plaques identified as positive by autoradiography were purified. Plaques with the largest inserts were sequenced. Additional 5' sequence was determine using 5' RACE. The cDNA and protein sequences for a T24 are shown in SEQ ID NOS: 1 and 2, respectively.

EXAMPLE 2

Recombinant Expression of T24

This example describes methods used to express T24 (SEQ ID NO: 2) recombinantly in insect cells.

Full-length T24, amino acids 1 through 225 (SEQ ID NO: 2), were expressed recombinantly using an insect cell expression system. A nucleic acid sequence encoding SEQ ID NO:

2 (nucleotides 33-710 of SEQ ID NO: 1) was cloned into pMT/BiP/V5-His A (Invitrogen, Carlsbad, Calif.) using standard molecular biology methods. Briefly, the vector, was cut with Bgl II and Kpn I and treated with phosphatase. The vector and insert were ligated, generating pMT/BiP/T24, and then transformed into *E. coli* TOP 10 cells (other cells can be used, such as *E. coli* DH5α-TI cells). Recombinant cells were selected with carbenicillin. The correct construction of the clone used for expression was confirmed by sequencing.

The vector generated above (pMT/BiP/T24) was purified from TOP10 cells (Invitrogen) using Qiagen midi-prep kit for plasmid DNA purification, and then transiently expressed in the insect cell line *D. melanogaster* Schneider 2 (S2) (ATCC, Manassas, Va.) using serum-free medium. Transfection was performed using calcium phosphate. After 72 hours, 500 µM copper sulfate was added to the culture to induce gene expression. The cultures were sampled at 24-hour intervals from 0 to 96 hours post-induction. The culture medium was centrifuged and separated into cell pellet and supernatant. Expression of T24 was observed in the supernatant beginning at 24 hours post-induction increasing at 48 hours and then holding steady at 72 and 96 hours post-induction.

To determine if recombinant T24 is immunoreactive with T24 antibodies, the following methods were used. The 96-hour supernatant generated above was loaded on a western blot at 0.625 µg/mm and strips made. The recombinant T24 protein migrates at a little less than 30 kDa. T24 was reactive with sera known to be infected with T soli/u. Because the genus *Echinococcus* is the most closely related genus to *Taenia*, serum from people infected with *Echinococcus* is potentially cross-reactive with *Taenia* antigens. However, recombinant T24 (as well as Triton-extracted T24 from Example 1) was not reactive with serum infected with *Echinococcus granulosus*. Therefore, *T. solium* T24 is species-specific even though its sequence is similar to *Echinococcus* sequences.

EXAMPLE 3

Immunoreactive Fragment of T24

This example describes methods used to generate a 92 amino acid fragment of T24, and methods used demonstrate that the fragment recognizes T24 antibodies and thus has immunoreative activity.

The hydrophilic portion of T24 (amino acids 104 through 195 of SEQ ID NO: 2), referred to herein as T24H, was recombinantly expressed using an insect cell expression system. This 92 amino acid fragment of T24 was amplified using Pfu polymerase. The forward primer was designed with a Bgl II restriction enzyme site, the reverse primer with a Kpn I site and two stop codons. The cloning was designed so that the insert would be in-frame with the BiP secretory signal of the vector. The vector, pMT/BiP/V5-His A (Invitrogen), was cut with Bgl II and Kpn I and treated with phosphatase. The vector and insert were ligated, generating pMT/BiP/T24H, and then transformed into *E. coli* TOP 10 cells. Recombinant cells were selected with carbenicillin. The correct construction of the clone used for expression was confirmed by sequencing.

The vector generated above was purified from TOP 10 cells as described in Example 2 and then transiently expressed in the insect cell line S2 (see Example 2) using serum-free medium. Transfection and induction were performed as described in Example 2. The cultures were sampled at 24-hour intervals from 0 to 96 hours post-induction. The culture medium was centrifuged and separated into cell pellet and supernatant. Expression of T24H was observed in the supernatant beginning at 24 hours post-induction with maximum expression at 96 hours.

To determine if T24H is immunoreactive with T24 antibodies, the following methods were used. The 96-hour supernatant generated above was loaded on a western blot at 0.625 μg/mm and strips made. The recombinant T24H protein migrates at about 10 kDa. T24H was reactive with sera known to be infected with *T. solium*, and with goat anti-native T24 antibodies. Out of 21 infection sera that react with native T24, 20 also reacted with recombinant T24H, indicating a sensitivity of 95%. In addition, out of 13 *T. solium* negative sera, 10 from other parasitic infections (EMEUS 377) and 3 NHS, 12 were negative indicating a specificity for T24H of 92%. These results indicate that T24H can distinguish *Taenia* from *Echinococcus.*

In addition, both recombinant full-length T24 (Example 2) and recombinant T24H were sensitive to reduction with DTT, similar to the native protein. After treatment of the recombinant proteins with DTT, all antibody reactivity with infection sera was lost.

In summary, these results demonstrate that a 92 amino acid fragment of T24 is immunoreactive with *T. solium* T24 antibodies with at least 95% sensitivity and at least 92% specificity.

EXAMPLE 4

Stable Expression of T24H

This example describes methods that were used to generate a stable cell line expressing recombinant T24H.

The recombinant vector, pMT/BiP/T24H (see Example 3), and the selection plasmid, pCoBlast (Invitrogen) which contains an ampicillin and a blasticidin gene, were co-transfected into S2 cells using the calcium-phosphate method. Blasticidin was added to the culture medium 96 hours post-transfection and the selective medium was maintained for 18 days. For expression, the stable cell line was induced with copper sulfate and the supernatant harvested at 96 hours. Western blot strips were made and tested with the same sera used to test the transiently expressed T24H described in Example 3. The results obtained using stably expressed T24H were the same as obtained with transiently expressed T24H.

EXAMPLE 5

Recombinant Expression in Insect Cells

Examples 2-4 describe expression of T24 and T24H in S2 insect cells, according to the manufacturer's instructions (Invitrogen). However, one skilled in the art will appreciate that other insect cells can be used. This example describes methods that can be used to express T24 and fragments thereof recombinantly in other insect cell lines.

The coding region of SEQ ID NO: 1, a fragment of SEQ ID NO: 1 (such as nucleotides 33-710 or 342-617), or variants of SEQ ID NO: 1 can be subcloned into the desired vector using standard molecular biology techniques.

For example, expression of T24 or T24H behind the honeybee melittin secretory signal or behind the BiP secretory signal can be performed in various insect cell lines, to allow secretion of the recombinant protein into the culture medium. The vector pMIB/V5-His A (Invitrogen) can be used to constitutively express T24 or T24H behind the honeybee melittin secretion signal in lepidopteran cells (such as Sf9, Sf21, High Five cells, all available from Invitrogen). Methods for generating the recombinant plasmids, transfecting them into insect cells (for example using lipid-mediated transfection), expressing, and purifying the recombinant protein are known in the art. In addition, instructions are provided by Invitrogen.

The vector pIZ/V5-His (Invitrogen) with BiP/T24H cloned into it can be used to constitutively express T24 or T24H behind the BiP secretion signal in any lepidopteran cell such as Sf9 and High Five cells. The sequence for BiP is from the vector pMT/BiP/V5-His. Methods for generating the recombinant plasmids, transfecting them into insect cells (for example using lipid-mediated transfection), expressing, and purifying the recombinant protein are known in the art. In addition, instructions are provided by Invitrogen.

A baculovirus transfer vector can also be used to produce recombinant T24 protein. Recombinant virus containing a T24 or T24H is generated by co-transfection of the transfer vector with Bac-N-Blue AcMNPV linear DNA, a modified baculovirus vector, in insect cells such as Sf9 cells. After purification of the recombinant virus, cells are infected and harvested at 96 hours post-infection as described above.

Total cell lysates from cultures transfected or infected with a recombinant T24 or T24H sequence can be analyzed by immunoblot as described in the above examples.

Other insect cells that can be used include, but are not limited to, *D. melanogaster* Kcl cells and gypsy moth cell line, IPLB-LdEIta (Ld).

EXAMPLE 6

Method for Detecting the Presence of T24 Antibodies in a Sample

This example describes methods that can be used to determine if a sample contains T24 antibodies. In some examples, the presence of T24 antibodies indicates that the subject has cysticercosis.

Recombinant or synthetic T24 proteins, such as those described in the examples above are purified to at least 50% purity, for example by resolving on SDS-PAGE, blotted onto a substrate (such as nitrocellulose or PVDF), and probed with a sample (such as sera) obtained from a subject having or suspected of having cysticercosis. The sample can be any biological sample, such as sera, saliva, or urine, or any sample in which T24 antibodies reside. If anti-cysticercosis T24 antibodies are present in the sample, they will specifically recognize and bind to the T24 proteins present in the substrate, thereby forming antibody-protein complexes. As noted above, full-length recombinant T24 migrates in SDS-PAGE at a little less than 30 kDa, while T24H migrates at about 10 kDa.

Detection of antibody-protein complexes can be achieved by labeling the antibody, protein, or both, with a detectable label. For example, following formation of antibody-protein complexes, the substrate containing the T24 protein can be probed with a secondary antibody containing a detectable label (such as a fluorophore). The secondary antibody can recognize the T24 protein or the anti-T24 antibody present in the biological sample. The detection of an interaction between a recombinant T24 protein and anti-T24 antibodies in the sample indicates that the subject has or had cysticercosis.

Ideally, little to no detectable reactivity with recombinant T24 is observed with a control sample from normal human sera (a subject not infected by *T. solium*) or a sample infected with another pathogen, such as *Echinococcus*.

EXAMPLE 7

Method for Detecting the Presence of T24 Sequences in a Sample

This example describes methods that can be used to determine if a sample contains T24 proteins or nucleic acid molecules. The disclosure of T24 protein and nucleic acid sequences allows those skilled in the art to use molecular biology methods to identify the presence of such sequences in a sample. In some examples, the presence of T24 proteins or nucleic acid molecules indicates that the subject has cysticercosis.

For example, primers can be generated based on SEQ ID NO: 1 that allow one to detect T24 sequences in a sample. In one example, the primers are used to amplify T24 sequences present in a sample, for example by using PCR or real time PCR.

In another example, probes containing a detectable label are generated based on SEQ ID NO: 1. Probes are contacted with a sample for a time sufficient to allow hybridization between the probe and a T24 nucleic acid sequence present in the sample. Resulting probe:T24 nucleic acid sequence complexes can then be detected. In some examples, the probe is conjugated to a solid substrate, such as a bead. In particular examples, nucleic acid molecules are isolated from a sample prior to exposing the nucleic acid sequences to a probe, for example by running the sample on a gel (such as an agarose or acrylamide gel). The gel is then contacted with a substrate such as nitrocellulose, to allow transfer of the nucleic acid sequences to the substrate. The substrate is contacted with the probe or a time sufficient to allow hybridization between the probe and a T24 nucleic acid sequence present in the substrate. Resulting probe:T24 nucleic acid sequence complexes can then be detected.

To detect T24 proteins present in a sample, antibodies that recognize T24 can be used (see Example 8). For example, proteins present in a sample can be purified, for example by running on an SDS-PAG, and transferred to a substrate. The substrate is then probed with an antibody that recognizes T24, thereby generating T24 protein-antibody complexes which are detected. The antibody can include a detectable label.

EXAMPLE 8

Production and Use of Antibodies

Monoclonal or polyclonal antibodies can be produced to a T24 protein, such as SEQ ID NO: 2, or variants, fragments, and fusions thereof (such as amino acids 104-195 of SEQ ID NO: 2). Optimally, antibodies raised against a T24 protein will specifically detect the protein. That is, antibodies raised against a T24 protein recognize and bind T24 protein but do not substantially recognize or bind to other proteins found in human or pig cells. The determination that an antibody specifically detects an protein is made using any standard immunoassay methods; for instance, Western blotting (Sambrook et al., 1989, *Molecular Cloning: A Laboratory Manual*, Cold Spring Harbor Laboratory, Cold Spring Harbor, N.Y.). Additionally, chimeric antibodies can be produced (for example, Morrison et al., *J. Bacteriol.* 159:870, 1984; Neuberger et al., *Nature* 312:604-8, 1984; and Takeda et al., *Nature* 314:452-4, 1985), as well as single-chain antibodies (for example, U.S. Pat. Nos. 5,476,786; 5,132,405; and 4,946,778).

The T24 protein can be obtained and purified from *T. solium*. Alternatively, T24 protein can be recombinantly generated (see Examples 2-5) or synthetically produced now that protein and nucleic acid sequences are known.

To determine that an antibody preparation (such as one produced in a mouse against a T24 protein) specifically detects the T24 protein by Western blotting, total cellular protein is extracted from cells (such as human or pig cells) and electrophoresed on a sodium dodecyl sulfate-polyacrylamide gel. The proteins are transferred to a membrane (for example, nitrocellulose) and the antibody preparation incubated with the membrane. After washing the membrane to remove non-specifically bound antibodies, the presence of specifically bound antibodies is detected by using an appropriate secondary antibody (such as an anti-mouse antibody or an anti-rabbit antibody) conjugated to a label (for example an enzyme such as alkaline phosphatase where application of substrate 5-bromo-4-chloro-3-indolyl phosphate/nitro blue tetrazolium results in the production of a dense blue compound by immuno-localized alkaline phosphatase).

Antibodies that specifically detect a T24 protein will, by this technique, be shown to bind to the protein band (such as the T24 band, which localizes at a given position on the gel determined by its molecular weight and phosphorylation; see Examples above). Non-specific binding of the antibody to other proteins may occur and may be detectable as a weak signal on the Western blot. The non-specific nature of this binding is recognized by one skilled in the art by the weak signal obtained on the Western blot relative to the strong primary signal arising from the specific antibody-T24 protein binding.

Substantially pure T24 proteins suitable for use as an immunogen is isolated as herein described, for example at least 50% pure by weight, for example at least 75%, at least 90%, or even at least 98% pure. Concentration of protein in the final preparation is adjusted, for example, by concentration on an Amicon filter device, to the level of a few µg/ml. Monoclonal or polyclonal antibody to the protein can then be prepared.

Monoclonal Antibody Production by Hybridoma Fusion

Monoclonal antibody to epitopes of a T24 protein can be identified, isolated and prepared from murine hybridomas using the method of Kohler and Milstein (*Nature* 256:495, 1975), using the human B-cell method (Kosbor et al., *Immunology Today* 4:72, 1983), or the EBV-hybridoma method (Cole et al., in *Monoclonal Antibodies and Cancer Therapy*, Alan R. Liss, Inc., pp. 77-96, 1983), or derivative thereof.

For example, a mouse is repetitively inoculated with a few µg of a T24 protein over a period of a few weeks. The mouse is sacrificed and antibody-producing cells of the spleen isolated. The spleen cells are fused using polyethylene glycol with mouse myeloma cells, and the excess unfused cells destroyed by growth of the system on selective media comprising aminopterin (HAT media). The fused cells are diluted and aliquots of the dilution placed in wells of a microtiter plate where growth of the culture is continued.

Antibody-producing clones are identified by detection of antibody in the supernatant fluid of the wells by immunoassay procedures, such as ELISA, as described by Engvall (*Enzymol.* 70:419, 1980), and similar methods. Selected positive clones can be expanded and their monoclonal antibody product harvested for use. Detailed procedures for monoclonal antibody production are described in Harlow and Lane (*Antibodies: A Laboratory Manual* 1988, Cold Spring Harbor Laboratory, New York). In addition, protocols for producing humanized forms of monoclonal antibodies (for therapeutic applications) and fragments of monoclonal antibodies are known in the art.

Polyclonal Antibody Production by Immunization

Polyclonal antiserum containing antibodies to heterogeneous epitopes of T24 protein can be prepared by immunizing suitable animals with the expressed protein, which can be unmodified or modified to enhance immunogenicity. Effective polyclonal antibody production is affected by many factors related to both the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis et al. (*J. Clin. Endocrinol. Metab.* 33:988-91, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In: *Handbook of Experimental Immunology*, Wier, D. (ed.). Chapter 19. Blackwell. 1973). Plateau concentration of antibody is usually in the range of 0.1 to 0.2 mg/ml of serum (about 12 µM). Affinity of the antisera for the antigen is determined by preparing competitive binding curves, as described, for example, by Fisher (*Manual of Clinical Immunology*, Chapter 42. 1980).

Antibodies Raised by Injection of a cDNA

Antibodies can be raised against a T24 protein by subcutaneous injection of a DNA vector expressing the protein into an animal, such as mice or rabbits. Delivery of the recombinant vector into the animal can be achieved using a hand-held form of the Biolistic system (Sanford et al., *Particulate Sci. Technol.* 5:27-37, 1987) described by Tang et al. (*Nature* 356:152-4, 1992). Expression vectors include recombinant vectors expressing a cDNA under transcriptional control of the human M-actin promoter or cytomegalovirus (CMV) promoter.

Labeled Antibodies

T24 antibodies can be conjugated with a label for their direct detection (see Chapter 9, Harlow and Lane, *Antibodies: A Laboratory Manual*. 1988). Exemplary labels include radiolabels, enzymes (such as alkaline phosphatase (AP) or HRP), calorimetric labels, chelating agents, fluorescent labels, colloidal gold, ligands (such as biotin), and chemiluminescent agents, and is chosen based on the method of detection available to the user. The method of producing these conjugates is determined by the reactive group on the label added.

For example, an antibody can be radiolabeled with iodine ($^{125}$I), which yields low-energy gamma and X-ray radiation. Briefly, 10 µg of protein in 25 µl of 0.5 M sodium phosphate (pH 7.50 is placed in a 1.5 ml conical tube. To this, 500 µC of Na$^{251}$, and 25 µl of 2 mg/ml chloramine T is added and incubated for 60 seconds at RT. To stop the reaction, 50 µl of chloramine T stop buffer is added (2.4 mg/ml sodium metabisulfite, 10 mg/ml tyrosine, 10% glycerol, 0.1% xylene cyanol in PBS). The iodinated antibody is separated from the iodotyrosine on a gel filtration column.

Uses for T24 Antibodies

T24 antibodies prepared according to these methods can be used in an assay to determine the presence of T24 or *T. solium* in a sample, such as a quantitative or semi-quantitative assay.

EXAMPLE 9

Antigenic Compositions

This example describes compositions that include T24 proteins (as well as fragments, fusions, and variants thereof) that can be used to stimulate an immune response in a subject. Stimulation of an immune response against a T24 protein, for example in a pig or human subject, can protect a subject against *T. solium* infection, cysticercosis, neurocysticercosis, or combinations thereof.

T24 recombinant or synthetic proteins can be present alone or with a pharmaceutically acceptable carrier. Pharmaceutically acceptable carriers include agents that aid in stimulation of the immune response, for example an adjuvant. Adjuvants are nonspecific immune stimulators that increase the immune readiness and aid in stimulating a higher level (titer) of serum antibodies that recognize the epitopic peptide sequences. Adjuvants include, for example, Freund's complete adjuvant, Freund's incomplete adjuvant, B30-MDP, LA-15-PH, montanide, saponin, aluminum hydroxide, alum, lipids, keyhole lympet protein, hemocyanin, a mycobacterial antigen, and combinations thereof. If the adjuvant is a lipid it may be linked to the epitopic peptide(s). A high titer of antibodies serves to protect a subject from the pathogen to which the antibodies are directed.

Other examples of pharmaceutically acceptable carriers include physiologically acceptable masses to which the T24 eptiope it attached, and in some examples, enhances the immune response. In one example, a mass is one or more amino acids or other moieties, such as a dimer, oligomer, or higher molecular weight polymer of a sequence of amino acids of a T24 epitope. In other words, a T24 epitope can be formed from naturally available materials or synthetically produced and can then be polymerized to build a chain of two or more repeating units so that the repeating sequences form both the carrier and the immunogenic polypeptide. Alternatively, additional amino acids can be added to one or both ends of a T24 peptide. Polysaccharides can also attached to the disclosed epitopes, and include those of molecular weight 10,000 to 1,000,000, such as starches, dextran, agarose, ficoll, or its carboxylmethyl derivative and carboxy methyl cellulose. Polyamino acids can also attached to the disclosed epitopes, and include, polylysine, polyalanyl polylysine, polyglutamic acid, polyaspartic acid and poly ($C_2$-$C_{10}$) amino acids.

Organic polymers can also attached to the disclosed T24 epitopes. Examples of such polymers include, but are not limited to, polymers and copolymers of amines, amides, olefins, vinyls, esters, acetals, polyamides, carbonates and ethers and the like. Generally, the molecular weight of these polymers will vary dramatically. The polymers can have from two repeating units up to several thousand, for example two thousand repeating units. The number of repeating units will be consistent with the use of the immunizing composition in a host animal. Generally, such polymers have a lower molecular weight, for example, between 10,000 and 100,000 kD (the molecular weight being determined by ultracentrifugation). Inorganic polymers can also be employed. These inorganic polymers can be inorganic polymers containing organic moieties. In particular, silicates and aluminum hydroxide can be used as carriers. Ideally, the carrier is an immunological adjuvant, such as muramyl dipeptide or its analogs.

Methods of administering the disclosed compositions to a subject are provided in Example 10.

Regardless of the exact formulation, T24 peptides (and nucleic acids encoding such epitopes), such as SEQ ID NOS: 1 and 2, or variants, fragments, fusions, and mixtures thereof, can be tested for their potential as an immunogenic molecule(s) or compositions with binding assays, in vitro cell culture techniques and in small mammal models. Proliferative assays can be used to measure the ability of T24 peptides to stimulate a T-cell response (PCT publication WO 02/22860). T-cells ($2\times10^4$) or irradiated peripheral blood mononuclear cells ($5\times10^4$) are seeded, in duplicate, into wells with or without about 200 µg/ml peptide (Hemmer, et al., 1998, *J. Pept. Res.* 52:338-45). Proliferation is measured by $^3$H-thymidine incorporation (Hemmer et al., 1997, *J. Exp. Med.* 185:1651-9).

The T24 peptides disclosed herein can also be tested in a cytotoxic T lymphocyte (CTL) assay (see, for example, Sette et al., 1994. *J. Immunol.* 153:5586-92, and PCT publication WO 01/55177). Briefly, the spleen of peptide immunized transgenic mice are collected aseptically 10 days after immunization and placed in 5 ml of cell medium (RMPI 1640, penicillin+streptomycin, 2% Hepes buffer, 10% Fetal calf serum) on ice. The splenocytes are cultured for 6 days in the presence of LPS blasts coated with 100 µg/ml of the peptide (stimulator cells) and then assayed for peptide-specific CTL activity by using EL4-A2 and EL4 cell lines in the presence or absence of the query peptides.

EXAMPLE 10

Administration of Therapeutic Agents

Administering a T24 peptide, nucleic acid molecule, or antibody of the present disclosure can be accomplished by any means known to the skilled artisan. For example, a pharmaceutically acceptable carrier can be provided for a T24 peptide, nucleic acid molecule, or antibody. Examples of pharmaceutically acceptable carriers include, but are not limited to, substances that are animal, vegetable, or mineral in origin, those that are physiologically acceptable and function to present a T24 epitope to the immune system. Thus, a wide variety of pharmaceutically acceptable carriers are acceptable, and include materials which are inert, or which have biological activity or promote an immune response.

Pharmaceutical preparations can contain only one type of therapeutic molecule, or can include a combination of several types of therapeutic molecules, such as other anti-cysticercosis or anti-helminthic agents, for example oxfendazole, albendazole, or praziquantel. In general, the nature of the pharmaceutically acceptable carrier will depend on the particular mode of administration being employed.

The pharmaceutical compositions disclosed herein can be prepared and administered in dose units. Solid dose units include tablets, capsules, transdermal delivery systems, and suppositories. For treatment of a subject, depending on activity of the compound, manner of administration, nature and severity of the disorder, age and body weight of the subject, different daily doses are necessary. Under certain circumstances, however, higher or lower daily doses may be appropriate. The administration of a therapeutic amount can be carried out both by single administration in the form of an individual dose unit or else several smaller dose units and also by multiple administration of subdivided doses at specific intervals.

The T24 peptides, nucleic acids, and antibodies and pharmaceutical compositions disclosed herein can be administered by any method used in the art, for example locally or systemically, such as topically, intravenously, orally, parenterally or as implants. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, Science 249:1527-33, 1990 (incorporated herein by reference).

In one example, T24 peptides, nucleic acids, and antibodies are administered to a subject in the presence of a lipid of lipoprotein. Liposomes are artificial membrane vesicles that are useful as delivery vehicles in vitro and in vivo. In one example, a liposome includes the desired molecule and is directed to the site of lymphoid cells, where the liposomes then deliver the selected therapeutic molecule. Large unilamellar vesicles (LUV), which range in size from 0.2-4.0 μm, can encapsulate a substantial percentage of an aqueous buffer containing large macromolecules. Nucleic acid molecules, proteins, and antibodies can be encapsulated within the aqueous interior and be delivered to cells in a biologically active form (Fraley et al., 1981, Trends Biochem. Sci. 6:77, 1981).

Liposomes can be formed from standard vesicle-forming lipids, which generally include neutral and negatively charged phospholipids (such as high-phase-transition-temperature phospholipids) in combination with a sterol, such as cholesterol. However, other lipids can be used, such as phosphatidyl compounds, for example phosphatidylglycerol, phosphatidylcholine, phosphatidylserine, phosphatidylethanolamine, sphingolipids, cerebrosides, and gangliosides. Other lipids that can be used include diacylphosphatidylglycerols, where the lipid moiety contains 14-18 carbon atoms, such as 16-18 carbon atoms, and is saturated. Additional phospholipids that can be used include, but are not limited to, egg phosphatidylcholine, dipalmitoylphosphatidylcholine and distearoylphosphatidylcholine.

The selection of lipids is generally guided by consideration of, for example, liposome size and stability of the liposomes in the blood stream. A variety of methods are available for preparing liposomes and are described, for example, in Szoka et al., 1980, Ann. Rev. Biophys. Bioeng 9:467 and U.S. Pat. Nos. 4,235,871, 4,501,728, 4,837,028, and 5,019,369. Particular lipid residues, such as palmitic acid or other uncharged fatty acid residues of different chain lengths and degrees of unsaturation, ranging from acetic to stearic acid as well as to negatively charged succinyl residues can be attached to the epitopic via the appropriate carboxylic acid anhydrides.

The lipids can be directly attached to a T24 epitopic peptide or indirectly through a linkage as described above. For example, a lipid can be attached directly to the amino terminus of the peptide or via a linkage such as Ser-Ser, Gly, Gly-Gly, or Ser.

The surface of a targeted delivery system can be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

For administration of T24 nucleic acid molecules, vectors can be used. In one example, the vector is a viral vector, such as an adenovirus, herpes virus, vaccinia, or an RNA virus such as a retrovirus. In one example, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV) can be utilized. A number of additional retroviral vectors can incorporate multiple genes. All of these vectors can transfer or incorporate a gene for a selectable marker so that transduced cells can be identified and generated. By inserting a nucleic acid sequence encoding a T24 peptide into the viral vector, along with another gene that encodes the ligand for a receptor on a specific target cell, for example, the vector is now target specific. Retroviral vectors can be made target specific by attaching, for example, a sugar, a glycolipid, or a protein. Targeting can be accomplished by using an antibody to target the retroviral vector. Those of skill in the art will know of, or can readily ascertain without undue experimentation, specific polynucleotide sequences that can be inserted into the retroviral genome or attached to a viral envelope to allow target specific delivery of the retroviral vector containing a nucleotide sequence encoding a T24 epitope.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines that have deletions of the packaging signal include, but are not limited to Q2, PA317, and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Another targeted delivery system for the therapeutic polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes.

Amounts effective for therapeutic use can depend on the severity of the disease and the age, weight, general state of the patient, and other clinical factors. Thus, the final determination of the appropriate treatment regimen will be made by the attending clinician. Dosages used in vitro can provide useful guidance in the amounts useful for in situ administration of the pharmaceutical composition, and animal models can be used to determine effective dosages for treatment of particular disorders. Various considerations are described, for example in Gilman et al., eds., *Goodman and Gilman: The Pharmacological Bases of Therapeutics,* 8th ed., Pergamon Press, 1990; and *Remington's Pharmaceutical Sciences,* 17$^{th}$ ed., Mack Publishing Co., Easton, Pa., 1990.

Typically, the dose range for a T24 protein is from about 0.1 μg/kg body weight to about 100 mg/kg body weight. Other suitable ranges include doses of from about 1 μg/kg to 10 mg/kg body weight. In one example, the dose is about 1.0 μg to about 50 mg, for example, 1 μg to 1 mg, such as 1 mg peptide per subject. The dosing schedule can vary from daily to as seldom as once a year, depending on clinical factors, such as the subject's sensitivity to the peptide and tempo of their disease. Therefore, a subject can receive a first dose of immunogenic T24 peptide, and then receive a second dose (or even more doses) at some later time(s), such as at least one day later, such as at least one week later, such as at least one month later. In one example, initial immunization can be followed by boosting dosages of from about 1 μg to 50 mg, for example, 1 μg to 500 μg, such as 1 μg to about 250 μg of peptide. A boosting regimen can be followed over weeks to months, depending upon the patient's response and condition by measuring specific immune activity in the patient's blood. In the case of a more aggressive disease it can be preferable to administer doses such as those described above by alternate routes including intravenously or intrathecally. Continuous infusion may also be appropriate.

Protein-based pharmaceuticals may be inefficiently delivered through ingestion. However, pill-based forms of pharmaceutical proteins can be administered subcutaneously, particularly if formulated in a slow-release composition. Slow-release formulations can be produced by combining the target protein with a biocompatible matrix, such as cholesterol. Another possible method of administering protein pharmaceuticals is through the use of mini osmotic pumps. As stated above a biocompatible carrier would also be used in conjunction with this method of delivery.

The disclosed peptides can also be used as diagnostic reagents. For example, a T24 immunogenic peptide can be used to determine the susceptibility of a particular individual to a treatment regimen that employs the peptide or related peptides. As diagnostic reagents, epitopic peptides can be helpful in modifying an existing treatment protocol or in determining a prognosis for an affected individual.

In view of the many possible embodiments to which the principles of our disclosure may be applied, it should be recognized that the illustrated embodiments are only particular examples of the disclosure and should not be taken as a limitation on the scope of the disclosure. Rather, the scope of the disclosure is in accord with the following claims. We therefore claim as our invention all that comes within the scope and spirit of these claims.

We claim:

1. A method for detecting *Taenia solium* (*T. solium*) antibodies in a sample comprising: contacting the sample with a composition comprising a purified peptide comprising the amino acid sequence of SEQ ID NO: 2, wherein the peptide binds to T24-*T. solium* antibodies, and wherein the purified peptide has a purity of at least 60% by weight; and detecting the formation of a complex between the peptide and a T24-*T.*

*solium* antibody in the sample, wherein a presence of an antibody—peptide complex indicates the presence of *T. solium* antibodies in the sample.

2. The method of claim 1, wherein the purified peptide consists of the amino acid sequence shown in SEQ ID NO: 2.

3. The method of claim 1, wherein the method further comprises contacting the sample with one or more of gp50, gp42, gp21, gp18, gp14, or gp13 larval *T. solium* proteins, to detect anti-gp50, -gp42, -gp21, -gp18, -gp14, or -gp13 antibodies, respectively.

4. The method of claim 1, wherein the peptide is encoded by a nucleic acid molecule comprising the nucleic acid sequence of SEQ ID NO: 1.

5. The method of claim 1, wherein the sample is obtained from a subject having or suspected of having cysticercosis.

6. The method of claim 5, wherein the subject is a human or pig.

7. A method for detecting *Taenia solium* (*T. solium*) antibodies in a sample comprising: contacting the sample with a composition comprising a purified peptide comprising amino acids 104-195 of SEQ ID NO: 2, wherein the peptide binds to T24-*T. solium* antibodies, and wherein the purified peptide has a purity of at least 60% by weight; and detecting the formation of a complex between the peptide and a T24-*T. solium* antibody in the sample, wherein a presence of an T24-*T. solium* antibody—peptide complex indicates the presence of *T. solium* antibodies in the sample.

8. The method of claim 7, wherein the purified peptide consists amino acids 104-195 of SEQ ID NO: 2.

9. The method of claim 1, wherein the method further comprises contacting the sample with one or more of gp50, gp42, gp21, gp18, gp14, or gp13 larval *T. solium* proteins, to detect anti-gp50, -gp42, -gp21, -gp18, -gp14, or -gp13 antibodies, respectively.

10. The method of claim 7, wherein the sample is obtained from a subject having or suspected of having cysticercosis.

11. The method of claim 10, wherein the subject is a human or pig.

* * * * *

SEQUENCE LISTING

<160> NUMBER OF SEQ ID NOS: 2

<210> SEQ ID NO 1
<211> LENGTH: 834
<212> TYPE: DNA
<213> ORGANISM: Taenia solium
<220> FEATURE:
<221> NAME/KEY: CDS
<222> LOCATION: (33)..(710)

<400> SEQUENCE: 1

```
ggcgttcgtt cacgcggaat caggacgccg ag atg ggt ctc tca tgc ggc ggt      53
                                    Met Gly Leu Ser Cys Gly Gly
                                     1               5 aat ttt ctc aag ttc ctt gtg ttc ttc ttc aac gcc att gtc ttc atc     101
Asn Phe Leu Lys Phe Leu Val Phe Phe Phe Asn Ala Ile Val Phe Ile
        10                  15                  20 gga ggt ggt gtg atc gcc gct ttt ggt atc tac ctc ttg gtt gag act     149
Gly Gly Gly Val Ile Ala Ala Phe Gly Ile Tyr Leu Leu Val Glu Thr
 25                  30                  35 aaa aaa tcc ggt ggt acg gtg tct ttg gtg ctt cct gct ttc ata act     197
Lys Lys Ser Gly Gly Thr Val Ser Leu Val Leu Pro Ala Phe Ile Thr
40                  45                  50                  55 gcc ttt ggt ctg ttg cta ttt ctg atc ggt ttc ctg ggc tgc ttc ggg     245
Ala Phe Gly Leu Leu Leu Phe Leu Ile Gly Phe Leu Gly Cys Phe Gly
                60                  65                  70 gct tgc tac aac aac aca tgc atg cta aaa acg ttc gca gcc ata gtc     293
Ala Cys Tyr Asn Asn Thr Cys Met Leu Lys Thr Phe Ala Ala Ile Val
            75                  80                  85 ggt att cta ctg gtc gcg gag att ata tgt gct att gtc ctc ctt gtc     341
Gly Ile Leu Leu Val Ala Glu Ile Ile Cys Ala Ile Val Leu Leu Val
        90                  95                 100 tat cgt cac gat ttc gtt cgc ctt gtt gga aaa gaa atg caa gaa gcg     389
Tyr Arg His Asp Phe Val Arg Leu Val Gly Lys Glu Met Gln Glu Ala
    105                 110                 115 att caa gag tta caa agc aaa cgt ctc tcg ggc tcc gac cct aca ctt     437
Ile Gln Glu Leu Gln Ser Lys Arg Leu Ser Gly Ser Asp Pro Thr Leu
120                 125                 130                 135 aaa gct ctg gag gaa ctg caa gca aag cta aaa tgc tgt gga ggt gtt     485
Lys Ala Leu Glu Glu Leu Gln Ala Lys Leu Lys Cys Cys Gly Gly Val
                140                 145                 150 ggc cca agt gat tgg aga gtc gct cct cca tca tgc tgc ggc aaa gaa     533
Gly Pro Ser Asp Trp Arg Val Ala Pro Pro Ser Cys Cys Gly Lys Glu
                155                 160                 165
```

```
agc gga tcc tgt aca agc cct tac caa act ggc tgt gct gaa gcc atg       581
Ser Gly Ser Cys Thr Ser Pro Tyr Gln Thr Gly Cys Ala Glu Ala Met
        170                 175                 180 tat aac gag atg aag gat tcc gct ctg gcc ttc ggc atc gta att atc       629
Tyr Asn Glu Met Lys Asp Ser Ala Leu Ala Phe Gly Ile Val Ile Ile
    185                 190                 195 gta atc ggc ctc att caa atc ggc gcc att atc tgc gct gca tgc ctg       677
Val Ile Gly Leu Ile Gln Ile Gly Ala Ile Ile Cys Ala Ala Cys Leu
200                 205                 210                 215 gct aag aag gtc agc gaa tat gag aag gtt tag gatgatgaaa atgaccaacc     730
Ala Lys Lys Val Ser Glu Tyr Glu Lys Val
                220                 225 aacccaccgt gtgtacttct tcgatgtaat acttatctcc gtatgagtga ataataccaa     790
gcatccgact cctcctgtcc taacaaaaaa aaaaaaaaaa aaaa                      834

<210> SEQ ID NO 2
<211> LENGTH: 225
<212> TYPE: PRT
<213> ORGANISM: Taenia solium

<400> SEQUENCE: 2

Met Gly Leu Ser Cys Gly Gly Asn Phe Leu Lys Phe Leu Val Phe Phe
1               5                   10                  15

Phe Asn Ala Ile Val Phe Ile Gly Gly Val Ile Ala Ala Phe Gly
            20                  25                  30

Ile Tyr Leu Leu Val Glu Thr Lys Lys Ser Gly Gly Thr Val Ser Leu
        35                  40                  45

Val Leu Pro Ala Phe Ile Thr Ala Phe Gly Leu Leu Leu Phe Leu Ile
    50                  55                  60

Gly Phe Leu Gly Cys Phe Gly Ala Cys Tyr Asn Asn Thr Cys Met Leu
65                  70                  75                  80

Lys Thr Phe Ala Ala Ile Val Gly Ile Leu Leu Val Ala Glu Ile Ile
                85                  90                  95

Cys Ala Ile Val Leu Leu Val Tyr Arg His Asp Phe Val Arg Leu Val
            100                 105                 110

Gly Lys Glu Met Gln Glu Ala Ile Gln Glu Leu Gln Ser Lys Arg Leu
        115                 120                 125

Ser Gly Ser Asp Pro Thr Leu Lys Ala Leu Glu Glu Leu Gln Ala Lys
    130                 135                 140

Leu Lys Cys Cys Gly Gly Val Gly Pro Ser Asp Trp Arg Val Ala Pro
145                 150                 155                 160

Pro Ser Cys Cys Gly Lys Glu Ser Gly Ser Cys Thr Ser Pro Tyr Gln
                165                 170                 175

Thr Gly Cys Ala Glu Ala Met Tyr Asn Glu Met Lys Asp Ser Ala Leu
            180                 185                 190

Ala Phe Gly Ile Val Ile Val Ile Gly Leu Ile Gln Ile Gly Ala
        195                 200                 205

Ile Ile Cys Ala Ala Cys Leu Ala Lys Lys Val Ser Glu Tyr Glu Lys
    210                 215                 220

Val
225
```